US011723909B2

(12) United States Patent
Yao et al.

(10) Patent No.: US 11,723,909 B2
(45) Date of Patent: *Aug. 15, 2023

(54) ORGANIC COMPOUNDS

(71) Applicant: INTRA-CELLULAR THERAPIES, INC., New York, NY (US)

(72) Inventors: Wei Yao, New Milford, NJ (US); Peng Li, New Milford, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 42 days.

This patent is subject to a terminal disclaimer.

(21) Appl. No.: 17/379,399

(22) Filed: Jul. 19, 2021

(65) Prior Publication Data

US 2022/0008423 A1  Jan. 13, 2022

Related U.S. Application Data

(63) Continuation of application No. 16/875,432, filed on May 15, 2020, now Pat. No. 11,096,944, which is a continuation of application No. 16/088,397, filed as application No. PCT/US2017/024137 on Mar. 24, 2017, now Pat. No. 10,688,097.

(60) Provisional application No. 62/313,629, filed on Mar. 25, 2016.

(51) Int. Cl.

| A61K 31/519 | (2006.01) |
|---|---|
| C07D 471/14 | (2006.01) |
| A61P 25/28 | (2006.01) |
| A61K 31/4985 | (2006.01) |
| A61K 45/06 | (2006.01) |
| A61P 25/00 | (2006.01) |
| A61P 25/18 | (2006.01) |
| A61P 25/24 | (2006.01) |

(52) U.S. Cl.
CPC ........ *A61K 31/519* (2013.01); *A61K 31/4985* (2013.01); *A61K 45/06* (2013.01); *A61P 25/00* (2018.01); *A61P 25/18* (2018.01); *A61P 25/24* (2018.01); *A61P 25/28* (2018.01); *C07D 471/14* (2013.01)

(58) Field of Classification Search
CPC .................................................. A61K 31/519
USPC ........................................................ 514/250
See application file for complete search history.

(56) References Cited

U.S. PATENT DOCUMENTS

| 4,530,840 | A | 7/1985 | Tice et al. |
|---|---|---|---|
| 5,114,976 | A | 5/1992 | Norden |
| 5,151,419 | A | 9/1992 | Perenyi et al. |
| 5,538,739 | A | 7/1996 | Bodmer et al. |
| 5,763,476 | A | 6/1998 | Delbressine et al. |
| 6,221,335 | B1 | 4/2001 | Foster |
| 6,440,710 | B1 | 8/2002 | Keinan et al. |
| 6,544,559 | B2 | 4/2003 | Mesens et al. |
| 6,548,493 | B1 | 4/2003 | Robichaud et al. |
| 6,552,017 | B1 | 4/2003 | Robichaud et al. |
| 6,603,008 | B1 | 8/2003 | Ando et al. |
| 6,699,852 | B2 | 3/2004 | Robichaud et al. |
| 6,713,471 | B1 | 3/2004 | Robichaud et al. |
| 7,071,186 | B2 | 7/2006 | Robichaud et al. |
| 7,081,455 | B2 | 7/2006 | Robichaud et al. |
| RE39,680 | E | 6/2007 | Robichaud et al. |
| 7,307,091 | B2 | 12/2007 | Alken et al. |
| 7,517,990 | B2 | 4/2009 | Ito et al. |
| 7,998,971 | B2 | 8/2011 | Barlow et al. |
| 8,309,722 | B2 | 11/2012 | Tornesch et al. |
| 8,598,119 | B2 | 12/2013 | Mates et al. |
| 8,648,077 | B2 | 2/2014 | Tornesch et al. |
| 8,791,138 | B2 | 7/2014 | Seeman et al. |
| 8,993,572 | B2 | 3/2015 | Mates et al. |
| 9,168,258 | B2 | 10/2015 | Mates et al. |
| 9,371,324 | B2 | 6/2016 | Mates et al. |
| 9,393,192 | B2 | 7/2016 | Yam et al. |
| 9,428,506 | B2 | 8/2016 | Mates et al. |
| 9,616,061 | B2 | 4/2017 | Mates et al. |
| 9,708,322 | B2 | 7/2017 | Li et al. |
| 9,745,300 | B2 | 8/2017 | Mates et al. |
| 9,956,227 | B2 | 5/2018 | Vanover et al. |
| 10,072,010 | B2 | 9/2018 | Li et al. |
| 10,077,267 | B2 | 9/2018 | Mates et al. |
| 10,117,867 | B2 | 11/2018 | Mates et al. |
| 10,322,134 | B2 | 6/2019 | Vanover et al. |
| 10,464,938 | B2 | 11/2019 | Tomesch et al. |
| 10,472,359 | B2 | 11/2019 | Li et al. |
| 10,597,394 | B2 | 3/2020 | Mates et al. |
| 10,702,522 | B2 | 3/2020 | Mates et al. |
| 10,688,097 | B2 | 6/2020 | Yao et al. |

(Continued)

FOREIGN PATENT DOCUMENTS

| WO | WO 2014/110322 | 7/2014 |
|---|---|---|
| WO | WO 2017/117514 | 7/2017 |
| WO | WO 2018/106916 | 6/2018 |

OTHER PUBLICATIONS

Baillie, T.A., "The Use of Stable Isotopes in Pharmacological Research," Pharmacology, 33(2): 81-132 (1981).

Browne, T.R., "Stable Isotope Techniques in Early Drug Development: An Economic Evaluation," J. Clin. Pharmacol., 38: 213-220 (1998).

Cherrah et al., "Study of Deuterium Isotope Effects on Protein Binding by Gas Chromatography/Mass Spectrometry. Caffeine Deuterated Isotopomers," Biomedical and Environmental Mass Spectrometry, 14: 653-657 (1987).

(Continued)

*Primary Examiner* — Taofiq A Solola
(74) *Attorney, Agent, or Firm* — Hoxie & Associates LLC

(57) ABSTRACT

The invention relates to particular substituted deuterated heterocycle fused gamma-carbolines, their prodrugs, in free, solid, pharmaceutically acceptable salt and/or substantially pure form as described herein, pharmaceutical compositions thereof, and methods of use in the treatment of diseases involving 5-HT2A receptor, serotonin transporter (SERT) and/or pathways involving dopamine D1/D2 receptor signaling systems, and/or the treatment of residual symptoms.

34 Claims, No Drawings

(56) References Cited

U.S. PATENT DOCUMENTS

| | | | |
|---|---|---|---|
| 10,844,061 | B2 | 11/2020 | Li et al. |
| 10,899,762 | B2 | 1/2021 | Mates et al. |
| 10,960,009 | B2 | 3/2021 | Vanover et al. |
| 10,960,010 | B2 | 3/2021 | Vanover et al. |
| 11,026,951 | B2 | 6/2021 | Mates et al. |
| 11,096,944 | B2 | 8/2021 | Yao et al. |
| 2009/0076159 | A1 | 3/2009 | Czarnik |
| 2010/0159033 | A1 | 6/2010 | Gant et al. |

OTHER PUBLICATIONS

Davis, et al., "ITI-007 demonstrates brain occupancy at serotonin 5-HT2A and dopamine D2 receptors and serotonin transporters using positron emission tomography in healthy volunteers," Psychopharmacology, vol. 232, pp. 2863-2872, (2015); DOI: 10.1007/s00213-015-3922-1.

Dyck et al., "Effects of Deuterium Substitution on the Catabolism of B-Phenylethylamine: An In Vivo Study," Journal of Neurochemistry, 46(2): 399-404 (1986).

Foster, A.B., "Deuterium Isotope Effects in the Metabolism of Drugs and Xenobiotics: Implications for Drug Design," 1985, Advances in Drug Research, vol. 14, pp. 1-40.

Gouyette, A., "Synthesis of Deuterium-labelled Elliptinium and its Use in Metabolic Studies," Biomedical and Environmental Mass Spectrometry, 15: 243-247 (1988).

Gramigna, J, "Lumateperone Safe, Effective for Depressive Symptoms Among Patients with Bipolar Disorders," American Society of Clinical Psychopharmacology Annual Meeting, Jun. 2, 2020, 3 pages.

Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.

Honma et al., "The Metabolism of Roxatidine Acetate Hydrochloride: Liberation of Deuterium form the Piperidine Ring during Hydroxylation," Drug Metabolism and Disposition, 15(4): 551-559 (1987).

Howland, R.H., "Deuterated Drugs," Journal of Psychosocial Nursing and Mental Health Services, 53(9): 13-16 (2015).

Khorana et al., "Gamma-Carbolines: Binding at 5-H15A Serotonin Receptors," Bioorganic & Medicinal Chemistry, 11: 717-722 (2003).

Lammers, et al., "Risperidone Long-acting Injection in Schizophrenia Spectrum Illnesses Compared to First Generation Depot Antipsychotics in an Outpatient Setting in Canada," BMC Psychiatry, vol. 13, No. 155, 9 pages, (2013); http://www.biomedcentral.com/1471-244X/13/155.

Lee et al., "Novel, Highly Potent, Selective 5-HT2A/D2 Receptor Antagonists as Potential Atypical Antipsychotics," Bioorganic & Medicinal Chemistry Letters, 13: 767-770 (2003).

Li et al., "Discovery of a Tetracyclic Quinoxaline Derivative as a Potent and Orally Active Multifunctional Drug Candidate for the Treatment of Neuropsychiatric and Neurological Disorders," Journal of Medicinal Chemistry, 57: 2670-2682 (2014).

Marek et al. Synergistic Action of 5-HT2A Antagonists and Selective Serotonin Reuptake Inhibitors in Neuropsychiatric Disorders. Neuropsychopharmacology, 2003. vol. 28, pp. 402-412. (Year: 2003).

O'Gorman, et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).

Perlis et al., "Clinical Features of Bipolar Depression Versus Major Depressive Disorder in Large Multicenter Trials", Am J Psychiatry, vol. 163, p. 225-231, (2006).

Rainer, M.K., "Risperidone long-acting injection: a review of its long term safety and efficacy," Neuropsychiatric Disease and Treatment, 4(5): 919-927 (2008).

Snyder et al., "Functional profile of a novel modulator of serotonin, dopamine, and glutamate neurotransmission," Psychopharmacology, 232: 605-621 (2015), Published online Aug. 2014, DOI 10.1007/s00213-014-3704-1.

Tohen, M., et al., "Efficacy of Olanzapine and Olanzapine-Fluoxetine Combination in the Treatment of Bipolar I Depression," Arch Gen Psychiatry, vol. 60, pp. 1079-1088, (2003).

Tung, R., "The Development of Deuterium-Containing Drugs," Innovations in Pharmaceutical Technology, 32: 1-4 (2010).

Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.

Wolen, R.L., "The Application of Stable Isotopes to Studies of Drug Bioavailability and Bioequivalence," J. Clin. Pharmacology, 26: 419-424 (1986).

Baba et al., "Studies on drug metabolism by use of isotopes. 23. Metabolic study of 1-butyryl-4-cinnamylpiperazine in the rat during development of tolerance by using two kinds of deuterium-labeled forms", J. Med. Chem., 21(6), pp. 525-529, (1978).

Cargnin, et al., "A primer of deuterium in drug design," Future Medicinal Chemistry, 11(16), 2039-42, (2019).

Harbeson, et al., "Deuterium Medicinal Chemistry: A New Approach to Drug Discovery and Development," Medchem News, 2: 8-22, (2014).

Russak, et al., "Impact of Deuterium Substitution on the Pharmacokinetics of Pharmaceuticals," Annals of Pharmacotherapy, 1-6, (2018).

Timmins, G.S., "Deuterated drugs: where are we now?", Expert Opin. Ther. Pat., 24(10):1067-75, (2014).

ORGANIC COMPOUNDS

CROSS-REFERENCE TO RELATED APPLICATIONS

This application is a continuation of U.S. patent application Ser. No. 16/875,432, filed on May 15, 2020, which is a continuation of U.S. patent application Ser. No. 16/088,397 filed on Sep. 25, 2018, now U.S. Pat. No. 10,688,097, which is a National Stage Entry under 35 U.S.C. § 371 of PCT Application No. PCT/US2017/024137, filed on Mar. 24, 2017, which claims priority to and the benefit of U.S. Provisional Patent Application Ser. No. 62/313,629, filed on Mar. 25, 2016, the contents of each of which are herein incorporated by reference in their entireties.

FIELD OF THE INVENTION

The invention relates to particular deuterated heterocycle fused gamma-carbolines, in free, pharmaceutically acceptable salt and/or substantially pure form as described herein, pharmaceutical compositions thereof, and methods of use in the treatment of diseases involving 5-HT$_{2A}$ receptor, serotonin transporter (SERT) and/or pathways involving dopamine $D_1/D_2$ receptor signaling systems, e.g., diseases or disorders such as anxiety, psychosis, schizophrenia, sleep disorders, sexual disorders, migraine, conditions associated with cephalic pain, social phobias, gastrointestinal disorders such as dysfunction of the gastrointestinal tract motility and obesity; depression and mood disorders associated with psychosis or Parkinson's disease; psychosis such as schizophrenia associated with depression; bipolar disorder; and other psychiatric and neurological conditions, as well as to combinations with other agents.

BACKGROUND OF THE INVENTION

Psychosis, particularly schizophrenia and schizoaffective disorder, affects an estimated 1-2% of the population worldwide. Schizophrenia is comprised of three phases: prodromal phase, active phase and residual phase. Prodromal phase is an early phase wherein subclinical signs and symptoms are observed. These symptoms may include loss of interest in usual pursuits, withdrawal from friends and family members, confusion, trouble with concentration, feeling of listlessness and apathy. Active phase is characterized by exacerbations of positive symptoms such as delusions, hallucinations and suspiciousness. Residual phase is characterized by negative symptoms such as emotional withdrawal, passive social withdrawal, and stereotyped thinking; and general psychopathological symptoms including active social avoidance, anxiety, tension, and somatic concerns. Residual phase symptoms also are often accompanied by depression, cognitive dysfunction and insomnia. Collectively, these residual phase symptoms are not well-treated by many antipsychotic drugs currently available on the market and therefore are usually observed after the active phase symptoms have subsided after treatment. This phase of the illness is when patients would like to return to more productive and fulfilling lives, but since the residual negative symptoms and cognitive impairment are not properly treated, it frustrates the return to such a function. There remains an urgent need for anti-psychotic agent, which can treat not just the active or acute phase symptoms, but also the residual phase symptoms of psychosis, e.g., schizophrenia. In addition, there is a need for medications to treat these symptoms that are free from undesirable side effects caused by off-target interactions with histamine H1 and muscarinic acetylcholine receptor systems.

Substituted heterocycle fused gamma-carbolines are known to be agonists or antagonists of 5-HT2 receptors, particularly 5-HT$_{2A}$ receptors, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with 5-HT$_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity.

PCT/US08/03340 (WO 2008/112280) and U.S. application Ser. No. 10/786,935 disclose methods of making substituted heterocycle fused gamma-carbolines and uses of these gamma-carbolines as serotonin agonists and antagonists useful for the control and prevention of central nervous system disorders such as addictive behavior and sleep disorders.

WO/2009/145900 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-HT$_{2A}$ receptors without affecting or minimally affecting dopamine $D_2$ receptors, thereby useful for the treatment of sleep disorders without the side effects of the dopamine $D_2$ pathways or side effects of other pathways (e.g., GABA$_A$ receptors) associated with conventional sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains.

Furthermore, it has been discovered that these particular substituted heterocycle fused gamma-carboline compounds (the compounds described herein below) are effective in treating not just acute symptoms, but also residual symptoms of psychosis. Therefore, the invention provides methods of using the particular substituted heterocycle fused gamma-carboline compounds (the compounds described herein below), either alone or as an adjunctive therapy for the treatment of residual symptoms of psychosis, particularly schizophrenia.

WO 2009/114181 discloses methods of preparing toluenesulfonic acid addition salt crystals of particular substituted heterocycle fused gamma-carbolines, e.g., toluenesulfonic acid addition salt of 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone.

WO 2011/133224 discloses prodrugs/metabolites of substituted heterocycle fused gamma-carboline for improved formulation, e.g., extended/controlled release formulation. This application discloses that heterocycle fused gamma-carboline N-substituted with a 4-fluorophenyl(4-hydroxy)butyl moiety are shown to have high selectivity for the serotonin transporter (SERT) relative to the heterocycle fused gamma-carboline containing 4-fluorophenylbutanone. The hydroxy group on these compounds, however, is interconverted to and from the ketone within the plasma and the brain, allowing it to serve as a reservoir for the 4-fluorophenylbutanone drug. While substituted heterocycle fused gamma-carbolines and their uses are known, our inventors have surprisingly found that particular substituted heterocycle fused gamma-carbolines, while less active in in-vitro tests, are inter-converted between these less active compounds and the highly active ketone drug within the plasma and the brain. Our inventors have further provided prodrugs of particular substituted heterocycle fused gamma-carbolines that have altered pharmacokinetic profile, e.g., altered mechanisms and/or rate of absorption and distribution, and therefore may be useful for an improved formulation and/or for controlling the duration of the effect of the drug in the body (e.g., for sustained- or controlled release).

WO 2013/155505 discloses compounds which block the in vivo inter-conversion between the hydroxy and the ketone, by incorporating an alkyl substituent on the carbon bearing the hydroxyl group, thus yielding compounds which antagonize 5-HT$_{2A}$ receptors and also inhibit serotonin re-uptake transporter.

The major routes of metabolism of the compounds previously disclosed are N-demethylation catalyzed by CYP 3A4, and ketone reduction catalyzed by ketone reductase. N-dealkylation by cytochrome oxidase enzymes is known to occur via an initial oxidation of one or more of the carbon atoms alpha to the nitrogen atom. The family of enzymes that catalyze ketone reduction is large and varied, and the mechanism has not been absolutely elucidated. It is of interest that, mechanistically, ketone reduction may operate either by way of the enol tautomer of the ketone or the keto tautomer.

WO 2015/154025 discloses generic deuterated heterocycle fused gamma carbolines for the purpose of reducing metabolic degradation by partially limiting metabolism of the ketone and/or the N-methyl substituent.

SUMMARY OF THE INVENTION

Applicants have unexpectedly discovered that the major routes of metabolism of fused heterocycle gamma carboline of Formula Q are by way of N-dealkylation and alpha-oxidation at the piperazine ring, and by reduction of the carbonyl, to yield the compounds of Formula Q-1, Q-2 and Q-3, as shown below:

Applicants have further found that the alcohol metabolite of Formula Q-2 retains significant pharmacological activity.

Without being bound by theory, the current invention provides compounds which specifically limit and/or prevent metabolism occurring by these pathways. Due to the very similar properties of deuterium (2H) atoms compared to normal hydrogen atoms ($^1$H), drug compounds in which deuterium is substituted for hydrogen are believed to generally have similar biological activity to the non-deuterated analog, but potentially with improved pharmacokinetic properties. The extent to which such a substitution will result in an improvement of pharmacokinetic properties without a too severe loss in pharmacologic activity is variable. Thus, in some circumstances, the resulting deuterated compound only a moderate increase in pharmacokinetic stability, while in other circumstances, the resulting deuterated compound may have significantly improved stability. Moreover, it may be difficult to predict with certainty the effects of simultaneous deuterium substitutions. These may or may not result in additive (synergistic) improvement in metabolic stability.

The current invention provides compounds containing a trideuterated N-methyl, and/or a di-deuterated methylene adjacent to the N-methyl. These novel compounds antagonize 5-HT$_2$A receptors, inhibit the serotonin re-uptake transporter, and modulate dopaminergic protein phosphorylation, in a like manner as to their natural hydrogen analogs. However, these compounds display an unexpectedly improved metabolic stability.

In the first embodiment, the invention provides a compound of Formula I:

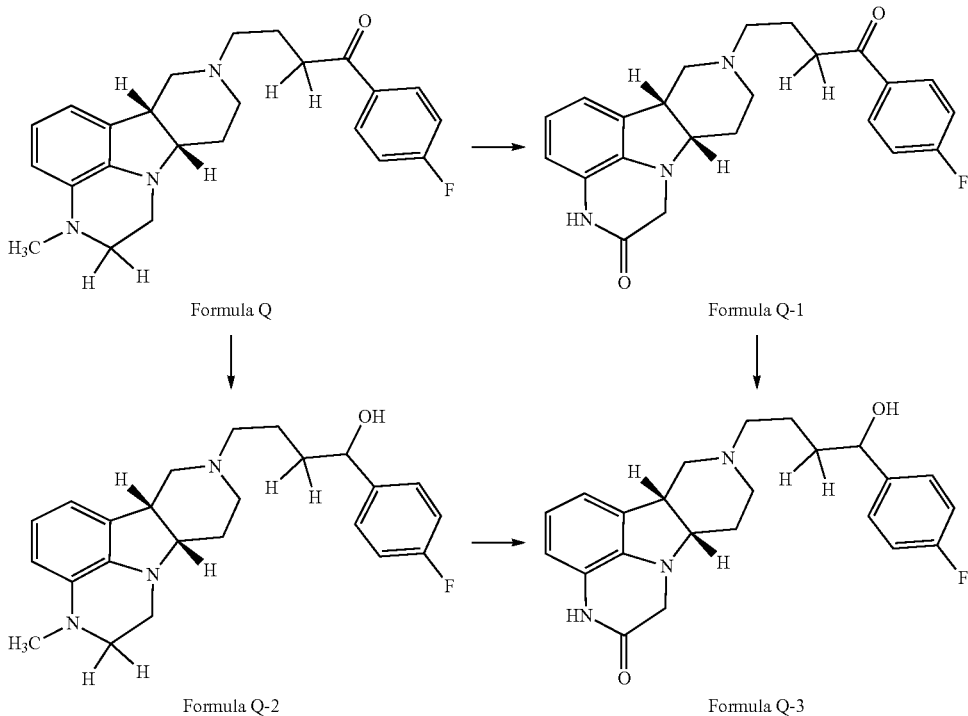

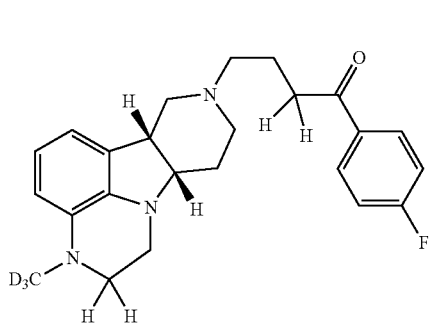

Formula I in free or salt form, e.g., in pharmaceutically acceptable salt form (e.g., tosylate).

In the second embodiment, the invention provides a compound of Formula II:

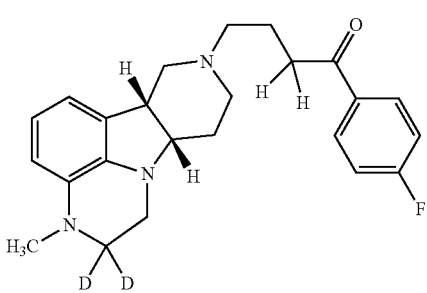

Formula II in free or salt form, e.g., in pharmaceutically acceptable salt form (e.g., tosylate).

In the third embodiment, the invention provides a compound of formula III:

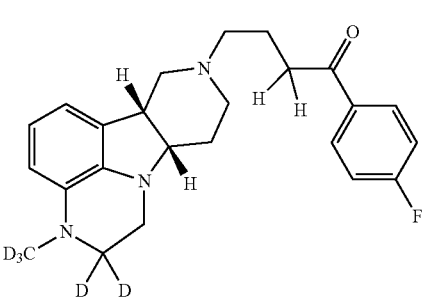

Formula III in free or salt form, e.g., in pharmaceutically acceptable salt form (e.g., tosylate).

In the fourth embodiment, the invention provides a compound of formula IV, in

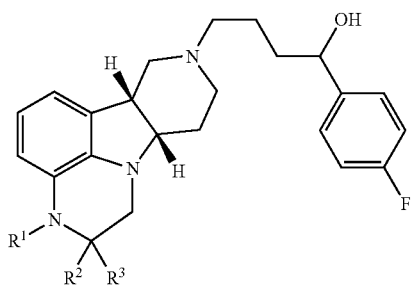

Formula IV wherein:
$R^1$ is $CH_3$ or $CD_3$;
$R^2$ and $R^3$ are either both H or both D;
provided that when $R^1$ is $CH_3$ $R^2$ and $R^3$ are both D;
free or salt form, e.g., in pharmaceutically acceptable salt form (e.g., tosylate).

In additional embodiments, the invention provides compounds as follows:
1.1 A compound of any of Formulas I to IV, wherein the compound is in free or pharmaceutically acceptable salt form;
1.2 A compound of Formula 1.1, wherein the salt form is an acid addition salt of a pharmaceutically acceptable acid;
1.3 A compound of Formula 1.2 wherein the acid is toluenesulfonic acid;
1.4 A compound of any of Formulas I to IV or 1.1-1.3, wherein the Compound is in substantially pure diastereomeric form (i.e., substantially free from other diastereomers);
1.5 A compound of any of Formulas I to IV or 1.1-1.4, wherein the Compound has a diastereomeric excess of greater than 70%, preferably greater than 80%, more preferably greater than 90% and most preferably greater than 95%;
1.6 A compound of any of Formulas I to IV or 1.1-1.5, wherein the compound has greater than natural incorporation of deuterium at the indicated deuterium positions of the structure (i.e., greater than 0.0156%);
1.7 A compound of any of Formulas I to IV or 1.1-1.6, wherein the compound has substantially greater than natural incorporation of deuterium at the indicated deuterium positions of the structure (e.g., greater than 0.1%, or greater than 0.5%, or greater than 1%, or greater than 5%);
1.8 A compound of any of Formulas I to IV or 1.1-1.7, wherein the compound has greater than 50% incorporation of deuterium at the indicated deuterated positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

In a second aspect, the invention provides a pharmaceutical composition comprising the compound of any of Formulas I to IV or 1.1-1.8 (the Compounds of the Invention), in free or pharmaceutically acceptable salt form, in admixture with a pharmaceutically acceptable diluent or carrier, e.g. to provide immediate release or to provide sustained or delayed release.

In a further embodiment of the second aspect, the Pharmaceutical Composition of the Invention is for a sustained or delayed release, e.g., a depot formulation. In one embodiment, the depot formulation comprises the Compounds of the Invention in a polymeric matrix. In another embodiment, the Compounds of the Invention are dispersed or dissolved within the polymeric matrix. In a further embodiment, the polymeric matrix comprises standard polymers used in depot formulations such as polymers selected from a polyester of a hydroxy fatty acid and derivatives thereof, or a polymer of an alkyl alpha-cyanoacrylate, a polyalkylene oxalate, a poly(ortho ester), a polycarbonate, a polyorthocarbonate, a poly(amino acid), a hyaluronic acid ester, and mixtures thereof. In a further embodiment, the polymer is selected from a group consisting of polylactide, poly d,l-lactide, poly glycolide, PLGA 50:50, PLGA 75:25, PLGA 85:15 and PLGA 90:10 polymer. In another embodiment, the polymer is selected from poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. In a particular embodiment, the polymeric matrix comprises poly (d,l-lactide-co-glycolide). Any of the Compositions hereinbefore described may be a pharmaceutical composition wherein said composition is in admixture with a pharmaceutically acceptable diluent or carrier.

The (Pharmaceutical) depot formulations as hereinbefore described are particularly useful for sustained or delayed release, wherein the Compounds of the Invention are released upon degradation of the polymeric matrix. These Compositions may be formulated for controlled- and/or sustained-release of the Compounds of the Invention (e.g., as a depot composition) over a period of up to 180 days, e.g., from about 14 to about 30 to about 180 days. For example, the polymeric matrix may degrade and release the Compounds of the Invention over a period of about 30, about 60 or about 90 days. In another example, the polymeric matrix may degrade and release the Compounds of the Invention over a period of about 120, or about 180 days.

In still another further embodiment, the Pharmaceutical Compositions of the Invention, particularly the depot compositions of the Invention, are formulated for administration by injection.

In a third aspect, the invention provides the Compounds of the Invention as hereinbefore described in an oral sustained or delayed release formulation. For example, the invention provides an osmotic controlled release oral delivery system (OROS) for delivery of the Compounds of the Invention, e.g. analogous to the systems described in WO 2000/35419 and EP 1 539 115 (U.S. Pub. No. 2009/0202631), the contents of each of which applications are incorporated by reference in their entirety. Therefore in one embodiment of this aspect, the invention provides a pharmaceutical composition or device comprising (a) a gelatin capsule containing a Compound of the Invention in free or pharmaceutically acceptable salt form or a Pharmaceutical Composition of the Invention, as hereinbefore described; (b) a multilayer wall superposed on the gelatin capsule comprising, in outward order from the capsule: (i) a barrier layer, (ii) an expandable layer, and (iii) a semipermeable layer; and (c) and orifice formed or formable through the wall. (Composition P.1)

In another embodiment of this aspect, the invention provides a composition comprising a gelatin capsule containing a liquid, the Compounds of the Invention in free or pharmaceutically acceptable salt form or a Pharmaceutical Composition of the Invention as hereinbefore described, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall. (Composition P.2)

In still another embodiment of the third aspect, the invention provides a composition comprising a gelatin capsule containing a liquid, the Compound of the Invention in free or pharmaceutically acceptable salt form or a Pharmaceutical Composition of the Invention as hereinbefore described, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice. (Composition P.3)

In still another embodiment of the third aspect, the invention provides a composition comprising a gelatin capsule containing a liquid, the Compound of the Invention in free or pharmaceutically acceptable salt form or a Pharmaceutical Composition of the Invention as hereinbefore described, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use. (Composition P.4). The expandable layer may be formed in one or more discrete sections, such as for example, two sections located on opposing sides or ends of the gelatin capsule.

In a particular embodiment of the third aspect, the Compound of the Inventions in the Osmotic-controlled Release Oral delivery System (i.e., in Composition P.1-P.4) are in a liquid formulation, which formulation may be neat, liquid active agent, liquid active agent in a solution, suspension, emulsion or self-emulsifying composition or the like.

Further information on Osmotic-controlled Release Oral delivery System composition including characteristics of the gelatin capsule, barrier layer, an expandable layer, a semi-permeable layer; and orifice may be found in WO 2000/35419, the contents of which are incorporated by reference in their entirety. Other Osmotic-controlled Release Oral delivery System for the Compound or the Pharmaceutical Composition of the Invention may be found in EP 1 539 115 (U.S. Pub. No. 2009/0202631), the contents of which are incorporated by reference in their entirety.

Therefore, in another embodiment of the third aspect, the invention provides a composition or device comprising (a) two or more layers, said two or more layers comprising a first layer and a second layer, said first layer comprises the Compound of the Invention, in free or pharmaceutically acceptable salt form, or a Pharmaceutical Composition as herein before described said second layer comprises a polymer; (b) an outer wall surrounding said two or more layers; and (c) an orifice in said outer wall. (Composition P.5)

Composition P.5 preferably utilizes a semi-permeable membrane surrounding a three-layer-core: in these embodiments the first layer is referred to as a first drug layer and contains low amounts of drug (e.g., the Compounds of the Invention) and an osmotic agent such as salt, the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet. (Composition P.6)

Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof. Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers.

In a particular embodiment, the invention provides Composition P.7, wherein the first drug layer comprising salt and the second drug layer containing no salt. Composition P.5-P.7 may optionally comprise a flow-promoting layer between the membrane and the drug layers. Compositions P.1-P.7 will generally be referred to as Osmotic-controlled Release Oral delivery System Composition.

In a fourth aspect, the invention provides a method (Method 1) for the treatment or prophylaxis of a central nervous system disorder, comprising administering to a patient in need thereof, a compound of Formulas I to IV or 1.1-1.8, in free or pharmaceutically acceptable salt form, or a pharmaceutical composition as hereinbefore described, and optionally wherein the compound of Formulas I to IV or 1.1-1.8 is administered in an effective dose which is lower than the effective dose for treatment of the same disorder using the compound of Formula Q.

In a further embodiment of the fourth aspect, the invention provides Method I wherein the method is further as described in the following formulae:

7.1 Method I, wherein the central nervous system disorder is one or more disorders associated with dementia, e.g., disorders associated with mild cognition impairment and dementing illnesses including senile dementia, Alzheimer's disease, Pick's disease, fronto-temporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoffs syndrome, cortico-basal degenerations and prion disease, autism and attention deficit hyperactivity disorder;

7.2 Method I or 7.1, wherein the disorders associated with dementia is selected from the group consisting of (1) behavioral or mood disorders such as agitation/irritation, aggressive/assaultive behavior, anger, physical or emotional outbursts; (2) psychosis; (3) depression; and (4) sleep disorders;

7.3 Method I or 7.1, wherein the central nervous system disorder is agitation/irritation, aggressive/assaultive behavior, anger, physical or emotional outbursts;

7.4 Method I, wherein the central nervous system disorder is a disorder selected from a group consisting of obesity, anxiety, depression (for example refractory depression and Major Depressive Disorder (MDD)), psychosis, schizophrenia, sleep disorders (particularly sleep disorders associated with schizophrenia and other psychiatric and neurological diseases), sexual disorders, migraine, conditions associated with cephalic pain, social phobias, agitation in dementia (e.g., agitation in Alzheimer's disease), agitation in autism and related autistic disorders, and gastrointestinal disorders such as dysfunction of the gastrointestinal tract motility;

7.5 Method I or any of 7.2-7.4, wherein the central nervous system disorder is a disorder involving serotonin 5-$HT_{2A}$, dopamine $D_1/D_2$ receptor system and/or serotonin reuptake transporter (SERT) pathways as similarly described in WO/2009/145900, the contents of which are herein incorporated by reference in their entirety;

7.6 Method I or any of Formulae 7.2-7.5, wherein the central nervous system disorder is a disorder involving serotonin reuptake transporter (SERT) pathways;

7.7 Method I or any of Formulae 7.2-7.6, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis, e.g., schizophrenia or Parkinson's disease; and (4) sleep disorders associated with psychosis, e.g., schizophrenia or Parkinson's disease; (5) depression; (6) anxiety; (7) post-traumatic stress disorder; or (8) impulse control disorder, e.g., intermittent explosive disorder;

7.8 Method I or any of Formulae 7.2-7.7, wherein the central nervous system disorder is psychosis, e.g., schizophrenia and said patient is a patient suffering from depression;

7.9 Method I or any of Formulae 7.2-7.8, wherein said patient is unable to tolerate the side effects of convention antipsychotic drugs, e.g., chlorpromazine, haloperidol, droperidol, fluphenazine, loxapine, mesoridazine, molindone, perphenazine, pimozide, prochlorperazine, promazine, thioridazine, thiothixene, trifluoperazine, clozapine, aripiprazole, olanzapine, quetiapine, risperidone and ziprasidone;

7.10 Method I or any of Formulae 7.2-7.9, wherein said patient is unable to tolerate the side effects of convention antipsychotic drugs, e.g., haloperidol, aripiprazole, clozapine, olanzapine, quetiapine, risperidone, and ziprasidone;

7.11 Method I or any of Formulae 7.2-7.10, wherein said disorder is depression and said patient is a patient suffering from psychosis, e.g., schizophrenia, or Parkinson's disease;

7.12 Method I or any of Formulae 7.2-7.6, wherein said disorder is sleep disorder and said patient is suffering from depression;

7.13 Method I or any of 7.2-7.6, wherein said one or more disorders is sleep disorder and said patient is suffering from psychosis, e.g., schizophrenia;

7.14 Method I or any of 7.2-7.6, wherein said one or more disorders is sleep disorder and said patient is suffering from Parkinson's disease;

7.15 Method I or any of 7.2-7.6, wherein said one or more disorders is sleep disorder and said patient is suffering from depression and psychosis, e.g., schizophrenia, or Parkinson's disease;

7.16 Method I or any of 7.1-7.6, wherein the central nervous system disorder is residual symptoms of psychosis, for example, schizophrenia (e.g., residual subtype), delusional disorder (e.g., somatic type), major depression with psychosis, bipolar disorder with psychotic symptoms, brief psychotic disorder, schizophreniform disorder, schizoaffective disorder or psychosis caused by a medical condition or substance use. Preferably, the patient is suffering from residual symptoms of schizophrenia;

7.17 Method I or any of 7.1-7.6, wherein the residual phase symptoms include: negative symptoms such as blunted affect, emotional withdrawal, poor rapport, passive or apathetic social withdrawal, difficulty in abstract thinking, lack of spontaneity and flow of conversation and stereotyped thinking; general psychopathology symptoms such as somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance; cognitive impairment and sleep disorders (e.g., insomnia);

7.18 Any of the foregoing methods, wherein the effective amount is 1 mg-1000 mg, preferably 2.5 mg-50 mg, still preferably 1-40 mg, e.g., 1-10 mg, e.g., 10 mg, 20 mg, or greater than 20 mg, e.g., 30 mg, 40 mg;

7.19 Any of the foregoing methods, wherein the effective amount is 1 mg-100 mg per day, preferably 2.5 mg-50 mg per day, still preferably 1-40 mg/day, e.g., 1-10 mg/day, e.g., 10 mg/day, 20 mg/day, or greater than 20 mg/day, e.g., 30 mg/day, 40 mg/day;

7.20 Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, e.g., levodopa, and anticholinergics;

7.21 Any of the foregoing methods wherein the patient suffers from Parkinson's disease;

7.22 Any of the foregoing methods wherein the patient does not respond to a selective serotonin re-uptake inhibitor, e.g. selected from one or more of citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Depex, Prozac, Fontex, Seromex, Seronil, Sarafem, Ladose, Motivest, Flutop, Fluctin (EUR), Fluox (NZ), Depress (UZB), Lovan (AUS), Prodep (IND)); fluvoxamine (Luvox, Fevarin, Faverin, Dumyrox, Favoxil, Movox); indalpine (Upstene); paroxetine (Paxil, Seroxat, Sereupin, Aropax, Deroxat, Divarius, Rexetin, Xetanor, Paroxat, Loxamine, Deparoc); sertraline (Zoloft, Lustral, Serlain, Asentra); vilazodone (Viibryd); or zimelidine (Zelmid, Nonnud);

7.23 Any of the foregoing methods wherein the patients is also receiving a selective serotonin re-uptake inhibitor, e.g. selected from one or more of citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Depex, Prozac, Fontex, Seromex, Seronil, Sarafem, Ladose, Motivest, Flutop, Fluctin (EUR), Fluox (NZ), Depress (UZB), Lovan (AUS), Prodep (IND)); fluvoxamine (Luvox, Fevarin, Faverin, Dumyrox, Favoxil, Movox); indalpine (Upstene); paroxetine (Paxil, Seroxat, Sereupin, Aropax, Deroxat, Divarius, Rexetin, Xetanor, Paroxat, Loxamine, Deparoc); sertraline (Zoloft, Lustral, Serlain, Asentra); vilazodone (Viibryd); or zimelidine (Zelmid, Normud);

7.24 Any of the foregoing methods wherein the patients is suffering from autistic spectrum disorder, e.g., autism or Asperger Syndrome;

7.25 Any of the foregoing methods wherein the patients is suffering from dementia, e.g., disorders associated with mild cognition impairment and dementing illnesses including senile dementia, Alzheimer's disease, Pick's disease, fronto-temporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoffs syndrome, cortico-basal degenerations and prion disease, autism and attention deficit hyperactivity disorder;

7.26 Any of the foregoing methods wherein the patient is also receiving a cholinesterase inhibitor (e.g., acetylcholinesterase inhibitor) or an N-Methyl D-Aspartate (NMDA) receptor antagonist, in free or pharmaceutically acceptable salt form;

7.27 Method 7.26, wherein the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form;

7.28 Method 7.26, wherein the cholinesterase inhibitor (e.g., acetylcholinesterase inhibitor) is donepezil in free or pharmaceutically acceptable salt form;

7.29 Method 7.26, wherein the NMDA receptor antagonist is memantine in free or pharmaceutically acceptable salt form;

7.30 Any of the foregoing methods further comprising administering one or more other therapeutic agents such as additional antipsychotic agents and/or antidepressive agents and/or hypnotic agents;

7.31 Method 7.30, wherein the one or more other therapeutic agents are selected from anti-depressive agents such as compounds that modulate GABA activity (e.g., enhances the activity and facilitates GABA transmission), a GABA-B agonist, a 5-HT modulator (e.g., a 5-HT1A agonist, a 5-HT2A antagonist, a 5-HT2A inverse agonist, etc.), a melatonin agonist, an ion channel modulator (e.g., blocker), a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug; and antipsychotic agents, e.g., atypical antipsychotic agents, in free or pharmaceutically acceptable salt form;

7.32 Method 7.30 or 7.31, wherein the one or more other therapeutic agents are antipsychotic agents, e.g., chlorpromazine, haloperidol, droperidol, fluphenazine, loxapine, mesoridazine, molindone, perphenazine, pimozide, prochlorperazine promazine, thioridazine, thiothixene, trifluoperazine, clozapine, aripiprazole, olanzapine, quetiapine, risperidone, ziprasidone, paliperidone, asenapine, lurasidone, iloperidone, caripra-zine, amisulpride, zotepine, sertindole, wherein the one or more other therapeutic agents are administered as an adjunct to the compound of Formulas I to IV or 1.1-1.8 or the compound of Formulas I to IV or 1.1-1.8 is an adjunct to the one or more other therapeutic agents.

In a particular embodiment of the fourth aspect, the invention provides a method (Method $I_P$) for the treatment or prophylaxis of a central nervous system disorder as hereinbefore described, comprising administering to a patient in need thereof:
- 7.4P a compound of Formulas I to IV or 1.1-1.8, in free or pharmaceutically acceptable salt form;
- 7.8P a Pharmaceutical or Depot Composition as hereinbefore described; or
- 7.11P Osmotic-controlled Release Oral delivery System Composition as hereinbefore described.

In a further embodiment of the fourth aspect, the invention provides Method $I_P$, wherein the method is further described in any one of formulae 7.1-7.32.

In a particular embodiment of the fourth aspect, the invention provides Method I, $I_P$, or any of 7.1-7.32, wherein the disorder is schizophrenia or sleep disorder.

In a particular embodiment of the fourth aspect, the invention provides Method I, $I_P$, or any of 7.1-7.32, wherein the disorder is depression or anxiety.

In a particular embodiment of the fourth aspect, the invention provides Method 1, $I_P$, or any of 7.1-7.32, wherein the disorder is post-traumatic stress disorder or an impulse control disorder, e.g., intermittent explosive disorder.

In a particular embodiment of the fourth aspect, the invention provides Method I, $I_P$, or any of 7.1-7.32, wherein the disorder is post-traumatic stress disorder or an impulse control disorder, e.g., intermittent explosive disorder in a patient suffering from dementia, e.g., senile dementia, Alzheimer's disease, Pick's disease, fronto-temporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoffs syndrome, cortico-basal degenerations, prion disease, autism and/or attention deficit hyperactivity disorder.

In still another embodiment of the fourth aspect, the invention provides Method 1, $I_P$, or any of 7.1-7.32, wherein the Depot Composition of the Invention is administered for controlled- and/or sustained-release of the Compounds of the Invention over a period of from about 14 days, about 30 to about 180 days, preferably over the period of about 30, about 60 or about 90 days. Controlled- and/or sustained-release is particularly useful for circumventing premature discontinuation of therapy, particularly for antipsychotic drug therapy where non-compliance or non-adherence to medication regimes is a common occurrence.

In a fifth aspect, the invention provides a method (Method II) for the prophylaxis or treatment one or more sleep disorders, agitation, aggressive behaviors, post-traumatic stress disorder and/or impulse control disorder, e.g., intermittent explosive disorder, comprising administering to a patient in need thereof a compound as described in the following formulae:
- 8.1 a compound of Formulas I to IV or 1.1-1.8, in free or pharmaceutically acceptable salt form;
- 8.2 a Pharmaceutical or Depot Composition as hereinbefore described;
- 8.3 Osmotic-controlled Release Oral delivery System Composition as hereinbefore described.

In one embodiment of the fifth aspect, the invention provides Method II or any of 8.1-8.3, wherein the disorder is sleep disorders. In another embodiment of the fifth aspect, the invention provides Method II, wherein the disorder is agitation, aggressive behaviors, post-traumatic stress disorder and/or impulse control disorder, e.g., intermittent explosive disorder.

In a further embodiment of the fifth aspect, the invention provides Method II, 8.1-8.3, wherein the sleep disorder includes sleep maintenance insomnia, frequent awakenings, and waking up feeling unrefreshed;
- 8.11 Any of the foregoing methods, wherein the sleep disorder is sleep maintenance insomnia;
- 8.12 Any of the foregoing methods, wherein the effective amount is 1 mg-10 mg per day, e.g., 1-5 mg, preferably 2.5-5 mg, per day, still preferably 10 mg per day;
- 8.13 Any of the foregoing methods, wherein the effective amount is 2.5 mg or 5 mg, per day or 10 mg per day;
- 8.14 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, e.g., receiving levodopa, and anticholinergics;
- 8.15 Any of the foregoing methods wherein the patient suffers from Parkinson's disease.

The Compounds of the Invention (e.g., a compound of Formulas I to IV or 1.1-1.8) provide effective treatment of $5\text{-HT}_{2A}$, SERT and/or $D_2$ receptor related disorders without or with minimal extrapyramidal side effects as similarly disclosed and claimed in WO 2009/145900, the contents of which are incorporated by reference in their entirety. Therefore, the Compounds of the Invention, the Pharmaceutical Compositions of the Invention or the Depot Compositions of the Invention may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the Compounds of the Invention may be simultaneously, sequentially, or contemporaneously administered with other anti-depressant, anti-psychotic, other hypnotic agents, and/or agents use to treat Parkinson's disease or mood disorders or dementia. In another example, side effects may be reduced or minimized by administering a Compound of the Invention in combination with one or more second therapeutic agents in free or salt form, wherein the dosages of (i) the second therapeutic agent(s) or (ii) both Compound of the Invention and the second therapeutic agent, are lower than if the agent/compound are administered as a monotherapy. In a particular embodiment, the Compounds of the Invention are useful to treat dyskinesia in a patient receiving dopaminergic medications, e.g., selected from levodopa and levodopa adjuncts (carbidopa, COMT inhibitors, MAO-B inhibitors), dopamine agonists, e.g., such as are used in the treatment of Parkinson's disease, and anticholinergics used to treat side effects of Parkinson's disease medications.

Therefore, in a sixth aspect, the current invention provides Method I or $I_P$, e.g., or any of formulae 7.1-7.32, or Method II or any of 8.1-8.15, further comprises one or more therapeutic agents selected from compounds that modulate GABA activity (e.g., enhances the activity and facilitates GABA transmission), a GABA-B agonist, a 5-HT modulator (e.g., a $5\text{-HT}_{1A}$ agonist, a $5\text{-HT}_{2A}$ antagonist, a $5\text{-HT}_{2A}$ inverse agonist, etc.), a melatonin agonist, an ion channel modulator (e.g., blocker), a serotonin-2 receptor antagonist/reuptake inhibitor (SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method I-A and II-A respectively).

In another embodiment of the sixth aspect, Method I-A and II-A, Method I, Method $I_P$, e.g., or any of formulae 7.1-7.32, or Method II or any of 8.1-8.15, further comprises one or more therapeutic agents selected from a cholinesterase inhibitor (e.g., acetylcholinesterase inhibitor) or an N-Methyl D-Aspartate (NMDA) receptor antagonist, in free or pharmaceutically acceptable salt form. In a specific embodiment, the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form. In a further embodiment, the cholinesterase inhibitor (e.g., acetylcholinesterase inhibitor) is donepezil in free or pharmaceutically acceptable salt form. In another embodiment, the NMDA receptor antagonist is memantine in free or pharmaceutically acceptable salt form.

In a further embodiment of the sixth aspect, the invention provides Method I-A or II-A as follows, further comprising one or more therapeutic agents.

9.1 Method I-A or II-A, wherein the therapeutic agent(s) is compounds that modulate GABA activity (e.g., enhances the activity and facilitates GABA transmission);

9.2 Method 1-A or 11-A or 9.1, wherein the GABA compound is selected from a group consisting of one or more of doxepin, alprazolam, bromazepam, clobazam, clonazepam, clorazepate, diazepam, flunitrazepam, fiurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals) and estazolam;

9.3 Method I-A or II-A, wherein the therapeutic agent is an additional $5HT_{2A}$ antagonist;

9.4 Method I-A or II-A or 9.3, wherein said additional $5HT_{2A}$ antagonist is selected from one or more of ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), and AVE8488 (Sanofi-Aventis, France); Method I-A or II-A, 9.3 or 9.4 additionally selected from pimavanserin (ACP-103) and pizotifen;

9.5 Method I-A or II-A, wherein the therapeutic agent is a melatonin agonist;

9.6 Method I-A or II-A or 9.5, wherein the melatonin agonist is selected from a group consisting of one or more of melatonin, ramelteon (ROZEREM®, Takeda Pharmaceuticals, Japan), VEC-162 (Vanda Pharmaceuticals, Rockville, Md.), PD-6735 (Phase II Discovery) and agomelatine;

9.7 Method I-A or II-A, wherein the therapeutic agent is an ion channel blocker;

9.8 Method I-A or II-A or 9.7, wherein said ion channel blocker is one or more of lamotrigine, gabapentin and pregabalin.

9.9 Method I-A or II-A, wherein the therapeutic agent is an orexin receptor antagonist;

9.10 Method I-A or II-A or 9.9, wherein the orexin receptor antagonist is selected from a group consisting of orexin, a 1,3-biarylurea, SB-334867-a (GlaxoSmithKline, UK), GW649868 (GlaxoSnithKline) and a benzamide derivative;

9.11 Method I-A or II-A, wherein the therapeutic agent is the serotonin-2 receptor antagonist/reuptake inhibitor (SARI);

9.12 Method I-A or TI-A or 9.11, wherein the serotonin-2 receptor antagonist/reuptake inhibitor (SARI) is selected from a group consisting of one or more Org 50081 (Organon-Netherlands), ritanserin, nefazodone, serzone and trazodone;

9.13 Method I-A or II-A, wherein the therapeutic agent is the 5HT1a agonist;

9.14 Method I-A or II-A or 9.13, wherein the $5HT_{1a}$ agonist is selected from a group consisting of one or more of repinotan, sarizotan, eptapirone, buspirone and MN-305 (MediciNova, San Diego, Calif.);

9.15 Method I-A or II-A, wherein the therapeutic agent is the neurokinin-1 drug;

9.16 Method I-A or II-A or 9.15, wherein the neurokinin-1 drug is Casopitant (GlaxoSmithKline);

9.17 Method I-A or II-A, wherein the therapeutic agent is an antipsychotic agent;

9.18 Method I-A or II-A or 9.17, wherein the antipsychotic agent is selected from a group consisting of chlorpromazine, haloperidol, droperidol, fluphenazine, loxapine, mesoridazine, molindone, perphenazine, pimozide, prochlorperazine promazine, thioridazine, thiothixene, trifluoperazine, clozapine, aripiprazole, olanzapine, quetiapine, risperidone, ziprasidone and paliperidone;

9.19 Method I-A or II-A, wherein the therapeutic agent is an anti-depressant;

9.20 Method I-A or II-A or 9.19, wherein the anti-depressant is selected from amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelazine sulfate, protriptyline, sertraline, tranylcypromine, trazodone, trimipramine, and venlafaxine;

9.21 Method T-A or IT-A, 9.17 or 9.18, wherein the antipsychotic agent is an atypical antipsychotic agent;

9.22 Method I-A or II-A, or any of 9.17-9.21, wherein the atypical antipsychotic agent is selected from a group consisting of clozapine, aripiprazole, olanzapine, quetiapine, risperidone, ziprasidone, and paliperidone;

9.23 Method I-A or II-A, wherein the therapeutic agent is selected from any of methods 9.1-9.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), AVE8488 (Sanofi-Aventis, France), repinotan, sarizotan, eptapirone, buspirone, MN-305 (MediciNova, San Diego, Calif.), melatonin, ramelteon (ROZEREM®, Takeda Pharmaceuticals, Japan), VEC-162 (Vanda Pharmaceuticals, Rockville, Md.), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelazine sulfate, protriptyline, sertraline, tranylcypromine, trazodone, trimipramine, venlafaxine, chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone, ziprasidone and paliperidone; In addition to the therapeutic agents listed herewith, Method I-A or II-A, is further selected from pimavanserin (ACP-103) and pizotifen;

9.24 Method I-A or II-A wherein the therapeutic agent is an H3 agonist;

9.25 Method I-A or 11-A, wherein the therapeutic agent is an H3 antagonist;

9.26 Method I-A or II-A, wherein the therapeutic agent is a noradrenergic agonist or antagonist;

9.27 Method I-A or II-A, wherein the therapeutic agent is a galanin agonist;

9.28 Method I-A or II-A, wherein the therapeutic agent is a CRH antagonist;

9.29 Method I-A or II-A, wherein the therapeutic agent is a human growth hormone;

9.30 Method I-A or II-A, wherein the therapeutic agent is a growth hormone agonist;

9.31 Method I-A or II-A, wherein the therapeutic agent is estrogen or an estrogen agonist;

9.32 Method I-A or II-A, wherein the therapeutic agent is 5-$HT_6$ receptor antagonist;

9.33 Method I-A or II-A, wherein the therapeutic agent is a neurokinin-1 drug;

9.34 Method I-A or II-A, wherein a therapeutic agent is combined with compounds of Formula (I) and the therapeutic agent is an anti-Parkinson agent such as L-dopa, co-careldopa, duodopa, stalova, Symmetrel, benzotropine, biperiden, bromocryiptine, entacapone, pergolide, pramipexole, procyclidine, ropinirole, selegiline and tolcapone;

9.35 Method I-A or II-A, wherein compounds of Formula (I) may be used to treat sleep disorders, depression, psychosis, or any combinations thereof, in patients suffering from the listed diseases and/or Parkinson's disease;

9.36 Method I-A or II-A, wherein the disorder is selected from at least one or more of psychosis, e.g., schizophrenia, depression, mood disorders, sleep disorders (e.g., sleep maintenance and/or sleep onset) or any combination of disorders thereof;

9.37 Any of the foregoing methods wherein the disorder is sleep disorder;

9.38 Any of the foregoing methods, wherein the disorder is sleep disorder associated with psychosis, e.g., schizophrenia or Parkinson's disease; in free or pharmaceutically acceptable salt form.

In another embodiment of the sixth aspect, the current invention provides Method $I_P$ or Method II as hereinbefore described, further comprises one or more therapeutic agents selected from compounds that modulate GABA activity (e.g., enhances the activity and facilitates GABA transmission), a GABA-B agonist, a 5-HT modulator (e.g., a 5-$HT_{1A}$agonist, a 5-$HT_{2A}$ antagonist, a 5-$HT_2$A inverse agonist, etc.), a melatonin agonist, an ion channel modulator (e.g., blocker), a serotonin-2 antagonist/reuptake inhibitor (SARIs), an orexin receptor agonist or antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method $I_P$-A and II-A respectively). In a further embodiment of this aspect, the invention provides Method $I_P$-A or II-A as similarly described in any one of formulae 9.1-9.38.

In still another embodiment of the sixth aspect, Method $I_P$ or Method II as hereinbefore described further comprises one or more therapeutic agents selected from a cholinesterase inhibitor (e.g., acetylcholinesterase inhibitor) or an N-Methyl D-Aspartate (NMDA) receptor antagonist, in free or pharmaceutically acceptable salt form. In a specific embodiment, the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form. In a further embodiment, the cholinesterase inhibitor (e.g., acetylcholinesterase inhibitor) is donepezil in free or pharmaceutically acceptable salt form. In another embodiment, the NMDA receptor antagonist is memantine in free or pharmaceutically acceptable salt form.

In a seventh aspect of the invention, the combination of a Compound of the Invention and one or more second therapeutic agents as described in Methods I-A, II-A or any of 9.1-9.38, may be administered as a Pharmaceutical Composition or a depot Composition as hereinbefore described. Similarly, the combination of a Compound of the Invention and one or more second therapeutic agents as described in Methods $I_p$-A, IL-A or any of 9.1-9.38, may be administered as a Pharmaceutical Composition or a depot Composition as hereinbefore described. The combination compositions can include mixtures of the combined drugs, as well as two or more separate compositions of the drugs, which individual compositions can be, for example, co-administered together to a patient.

In a particular embodiment, Methods I-A, II-A, $I_p$-A, II-A or any of 9.1-9.38 comprises administering to a patient in need thereof, a Compound of the Invention in combination with an atypical antipsychotic agent, e.g., a compound selected from clozapine, aripiprazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Methods I-A, II-A, Methods $I_p$-A, II-A or any of 9.1-9.38 comprises administering to a patient in need thereof, a Compound of the Invention in combination with an anti-depressant, e.g., amitriptyline, amoxapine, bupropion, citalopram, cloniprimine, desipramine, doxepin, duloxetine, escitalopram, fluoxetine, fluvoxanine, imipramine, isocarboxazid, maprotiline, mirtazapine, nefazodone, nortriptyline, paroxetine, phenelazine sulfate, protriptyline, sertraline, tranylcypromine, trazodone, trimipramine, or venlafaxine, in free or pharmaceutically acceptable salt form. Alternatively, the anti-depressant may be used as an adjunct medication in addition to the compounds of the Invention.

In still another embodiment, Methods I-A, II-A, $I_p$-A, II-A or any of 9.1-9.38 comprises administering to a patient in need thereof, a Compound of the Invention in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals), estazolam or any combinations thereof, in free or pharmaceutically acceptable salt form.

In another particular embodiment, Methods I-A, II-A, I$_P$-A, II-A or any of 9.1-9.38 comprises administering to a patient in need thereof, a Compound of the Invention in combination with doxepin in free or pharmaceutically acceptable salt form. Dosages of doxepin can vary in any range known to a person of ordinary skill in the art. In one example, a 10 mg dose of doxepin may be combined with any dosage of a compound of the Invention.

In another embodiment, Methods I-A, II-A, I$_P$-A, II-A or any of 9.1-9.38 comprises administering to a patient in need thereof, a Compound of the Invention in combination (including as part of a daily dosage regimen) with an atypical stimulant, e.g., a modafinil, adrafRnil, or armodafinil. A regimen incorporating a Compound of the Invention with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

In an eighth aspect, the invention provides use of a compound as described in the following formulae:
  11.1 Compound of Formula I or any of formulae 1-1.9, in free or pharmaceutically acceptable salt form;
  11.2 a Pharmaceutical Composition as hereinbefore described;
  11.3 Depot Composition as hereinbefore described; or
  11.4 Osmotic-controlled Release Oral delivery System Composition as hereinbefore described,
(in the manufacture of a medicament) for the treatment or prophylaxis of one or more disorders as disclosed hereinbefore, e.g., in any of Method I, any of 7.1-7.32, Method II, any of 8.1-8.15, Methods I-A, II-A, any of 9.1-9.38, Method I$_P$, Methods I$_P$-A, or any methods described in the sixth or seventh aspect of the invention.

In a ninth aspect, the invention provides a pharmaceutical composition as hereinbefore described, e.g., in the following formulae:
  12.1 a Pharmaceutical Composition as hereinbefore described;
  12.2 Depot Composition as hereinbefore described; or
  12.3 Osmotic-controlled Release Oral delivery System Composition as hereinbefore described,
for use in the treatment or prophylaxis of one or more disorders as disclosed hereinbefore, e.g., in any of Method I, any of 7.1-7.32, Method II, any of 8.1-8.15, Methods I-A, II-A, any of 9.1-9.38, Method I$_P$, Methods I$_P$-A, or any methods described in the sixth or seventh aspect of the invention.

In particular embodiments of any of the methods hereinbefore described, including any preceding embodiments of the fourth aspect (including Method I and any of Methods 7.1-7.32), the fifth aspect (including Method 11 and any of Methods 8.1-8.15), Method I$_P$, Methods I$_P$-A, the sixth aspect (including Method I-A, II-A and any of Methods 9.1-9.38), and the seventh aspect, the disorders and conditions referred to have their meaning as defined in the American Psychiatric Association's Diagnostic and Statistical Manual of Mental Disorders, Fifth Edition (DSM-V) (2013).

In other particular embodiments of any of the methods hereinbefore described, including any preceding embodiments of the fourth aspect (including Method I and any of Methods 7.1-7.32), the fifth aspect (including Method II and any of Methods 8.1-8.15), Method I$_P$, Methods I$_P$-A, the sixth aspect (including Method I-A, II-A and any of Methods 9.1-9.38), and the seventh aspect, the disorders and conditions referred to have their meaning as defined in the World Health Organization's International Classification of Diseases, Tenth Revision (ICD-10), Chapter V (Mental and Behavioral Disorders) (1992).

DETAILED DESCRIPTION OF THE INVENTION

If not otherwise specified or clear from context, the following terms as used herein have the following meetings:
  a. "Residual symptoms" as used herein include negative symptoms and general psychopathology symptoms as described in the Positive and Negative Symptom Scale (PANSS) for Schizophrenia described in Kay et al., *Schizophr. Bull.* (1987) 13(2):261-276, the contents of which are incorporated by reference in their entirety. Negative symptoms include: blunted affect, emotional withdrawal, poor rapport, passive/apathetic social withdrawal, difficulty in abstract thinking, lack of spontaneity and flow of conversation and stereotyped thinking. General psychopathology symptoms include: somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance. Residual symptoms may also include depression, cognitive impairment and sleep disorders (e.g., insomnia). Of these residual symptoms, the compounds of the invention are particularly useful for the treatment of passive social withdrawal, stereotyped thinking, somatic concerns, anxiety, tension, active social avoidance and depression. Therefore, the compounds of the present invention are particularly useful in improving social integration and social function in patients suffering from schizophrenia. Treatment of these residual symptoms is also particularly effective in schizophrenic patients also suffering from depression.
  b. As used in a formula, for example in the structure of any of Formulas I-IV or 1.1-1.8, and in a term such as "CD$_3$", "D" refers to an atom of hydrogen which contains more than the natural abundance of the isotope deuterium ($^2$H). All naturally occurring chemical compound include hydrogen atoms containing approximately 0.0156 atom % deuterium for every hydrogen atom. The use of "D" and "deuterium" in the present disclosure refers to any enrichment of the amount of deuterium above this natural abundance, for example, above 0.1%, or above 1%, up to any value short of 100% (e.g., 99%, or 99.9%, or 99.99%, or 99.999%). The use of "H" as a hydrogen atom refers to a hydrogen atom in a chemical structure containing not more than the natural abundance of deuterium, e.g., not more than 0.0156 atom % deuterium.

Unless otherwise indicated, the Compounds of the Invention, e.g., a compound of Formulas I to IV or 1.1-1.8, may exist in free or salt, e.g., as acid addition salts, form. An acid-addition salt of a compound of the invention which is sufficiently basic, for example, an acid-addition salt with, for example, an inorganic or organic acid. In a particular embodiment, the salt of the Compounds of the Invention is a toluenesulfonic acid addition salt.

The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention, and are therefore also included.

The Compounds of the Invention may comprise one or more chiral carbon atoms. The compounds thus exist in individual isomeric, e.g., enantiomeric or diastereomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diastereomeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

Alternatively and/or additionally, the Compounds of the Invention may be included as a depot formulation, e.g., by dispersing, dissolving or encapsulating the Compounds of the Invention in a polymeric matrix as described in the second and third aspect, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxy-fatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethylene glycol copolymer or polyglycolic acid-polyethylene glycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly (lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl-(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 daltons, preferably about 150,000 daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e. g., glucose or, e. g., mannitol. These esters are known and described in GB 2,145,422 and in U.S. Pat. No. 5,538,739, the contents of which are incorporated by reference.

The star polymers may be prepared using polyhydroxy compounds, e. g., polyol, e. g., glucose or mannitol as the initiator. The polyol contains at least 3 hydroxy groups and has a molecular weight of up to about 20,000 Daltons, with at least 1, preferably at least 2, e. g., as a mean 3 of the hydroxy groups of the polyol being in the form of ester groups, which contain polylactide or co-polylactide chains. The branched polyesters, e. g., poly (d, l-lactide-co-glycolide) have a central glucose moiety having rays of linear polylactide chains.

The depot composition of the invention as hereinbefore described may comprise the polymer in the form of microparticles or nanoparticles, or in a liquid form, with the Compounds of the Invention dispersed or encapsulated therein. "Microparticles" is meant solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

In a particular embodiment, the Compound of the Invention is formulated into microparticles of an appropriate size to allow slow release kinetics after intramuscular injection.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. Nos. 4,389,330 and 4,530,840, the contents of which are incorporated by reference.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of the Invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the Compounds of the Invention incorporated in the microparticles usually ranges from about 1 wt % to about 90 wt. %, preferably 30 to 50 wt. %, more preferably 35 to 40 wt. %. By weight % is meant parts of the Compounds of the Invention per total weight of microparticle.

The pharmaceutical depot may comprise a pharmaceutically-acceptable diluent or carrier, such as a water miscible diluent or carrier.

Details of Osmotic-controlled Release Oral delivery System composition may be found in EP 1 539 115 (U.S. Pub. No. 2009/0202631) and WO 2000/35419, the contents of each of which are incorporated by reference in their entirety.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular Compounds of the Invention used, the mode of administration, and the therapy desired.

Compounds of the Invention may be administered by any satisfactory route, including orally, parenterally (intravenously, intramuscular or subcutaneous) or transdermally, but are preferably administered orally. In certain embodiments, the Compounds of the Invention, e.g., in depot formulation, is preferably administered parenterally, e.g., by injection.

In general, satisfactory results for Method I or any of formulae 7.1-7.32 or Method $I_P$ or use of the Compounds of the Invention as hereinbefore described, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; and (4) sleep disorders associated with psychosis, e.g., schizophrenia, or Parkinson's disease, as set forth above are indicated to be obtained on oral administration at dosages of the order from about 1 mg to 100 mg once daily, preferably about 2.5 mg-50 mg, e.g., 2.5 mg, 5 mg, 10 mg, 20 mg, 30 mg, 40 mg or 50 mg, once daily, preferably via oral administration.

Satisfactory results for Method II or any of 8.1-8.15, Method II or use of the Compounds of the Invention as hereinbefore described, e.g. for the treatment of sleep disorder alone or agitation, aggressive behaviors, post-traumatic stress disorder or impulse control disorder alone, e.g., intermittent explosive disorder alone are indicated to be obtained on oral administration at dosages of the order from about 1 mg-10 mg once daily, e.g., about 2.5 mg-5 mg, e.g., 2.5 mg, 3 mg, 4 mg, 5 mg or 10 mg, of a Compound of the Invention, in free or pharmaceutically acceptable salt form, once daily, preferably via oral administration.

Satisfactory results for Method I-A or any of 9.1-9.38 or Method $I_P$-A are indicated to be obtained at less than 100 mg, preferably less than 50 mg, e.g., less than 40 mg, less than 30 mg, less than 20 mg, less than 10 mg, less than 5 mg, less than 2.5 mg, once daily. Satisfactory results for Method 11-A or any of 9.1-9.38 are indicated to be obtained at less than 10 mg, e.g., less than 5 mg or, preferably less than 2.5 mg.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. In a particular embodiment, the dosage regimen for depot composition includes an initial oral immediate dose along with depot release so as to provide a steady-state blood level of the drug. Duration of action of the Compounds of the Invention may be controlled by manipulation of the polymer composition, i.e., the polymer:drug ratio and microparticle size. Wherein the composition of the invention is a depot composition, administration by injection is preferred.

The pharmaceutically acceptable salts of the Compounds of the Invention can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069.

Pharmaceutical compositions comprising Compounds of the Invention may be prepared using conventional diluents or excipients (an example include, but is not limited to sesame oil) and techniques known in the galenic art. Thus oral dosage forms may include tablets, capsules, solutions, suspensions and the like.

All references herein to dosage, dosage rate or therapeutically effect amount of a Compound or Composition of the Invention refers to the equivalent free-base moiety in the dosage, excluding any salts.

Methods of Making the Compounds of the Invention

The intermediates of the Compounds of the Invention may generally be prepared as described in in WO PCT/US08/03340 (WO 2008/112280); U.S. application Ser. No. 10/786,935; U.S. Pat. Nos. 6,548,493; 7,238,690; 6,552,017; 6,713,471; 7,183,282; U.S. RE39680, and U.S. RE39679, and WO 2015/154025, the contents of each of which are incorporated by reference in their entirety. Salts of the Compounds of the Invention may also be prepared as similarly described in U.S. Pat. Nos. 6,548,493; 7,238,690; 6,552,017; 6,713,471; 7,183,282; U.S. RE39680; U.S. RE39679; and WO 2009/114181, the contents of each of which are incorporated by reference in their entirety.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

Example 1

1-(4-Fluorophenyl)-4-((6bR,10aS)-3-methyl-d$_3$-2,3,6b,7,10,10a-hexahydro-1H-pyrido[3',4':4,5]pyrrolo[1,2,3-de]quinoxalin-8(9H)-yl)butan-1-one p-toluenesulfonate

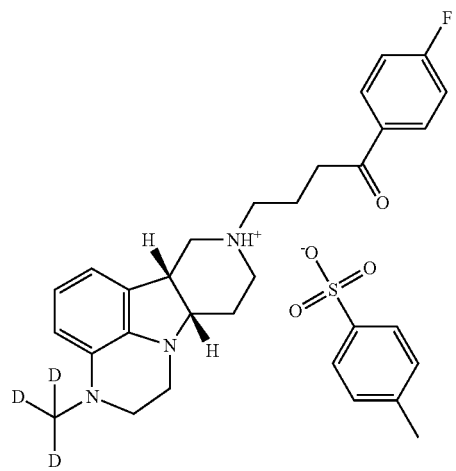

To a suspension of (6bR, 10aS)-2-oxo-2,3,6b,9,10,10a-hexahydro-1H,7H-pyrido[3',4':4,5]pyrrolo[1,2,3-de]quinoxaline-8-carboxylic acid ethyl ester (4.27 g, 14.2 mmol) in DMF (70 mL) is added NaH (560 mg, 95%, 21.3 mmol) in batches at room temperature. The suspension is then stirred at room temperature for 30 min until a clear light red solution is obtained. After the solution is cooled to 0-5° C., CD$_3$I (982 µL, 17.0 mmol) in DMF (1 mL) is added. The reaction mixture is stirred at 0-5° C. until all of the starting material is consumed. After quenching by ice, the mixture is acidified to pH of 3-5 with HCl (12 N, 0.2 mL) and then concentrated under reduced pressure. The obtained residue is suspended in a mixture of dichloromethane (100 mL) and H$_2$O (50 mL) and then adjusted to pH≥14 with 50% NaOH. The organic phase is separated and then concentrated to dryness to give 5 g of the crude (6bR,10aS)-ethyl 3-methyl-d3-2-oxo-2,3,6b,7,10,10a-hexahydro-1H-pyrido[3',4':4,5]pyrrolo[1,2,3-de]quinoxaline-8(9H)-carboxylate as a brown solid, which is used directly in the next step without further purification. MS (ESI) m/z 319.2 [M+H]$^+$.

To a stirred solution of (6bR, 10aS)-3-methyl-2-oxo-2,3,6b,9,10,10a-hexahydro-1H,7H-pyrido[3',4':4,5]pyrrolo[1,2,3-de]quinoxaline-8-carboxylic acid ethyl ester (3.09 g, 9.71 mmol) in THF (20 mL) is added BH$_3$ in THF (50 mL, 1.0 M, 50.0 mmol) at room temperature. The mixture is stirred at room temperature for 36 h, and then is cooled to 0-5° C., followed by quenching with MeOH (5 mL). The solvents are removed under reduced pressure to give a light yellow residue. To the residue is added HCl (12 N, 35 mL) at room temperature. The resulting mixture is stirred at 95° C. for 30 h, cooled to 0-5° C. and is then adjusted to a pH of 14 with NaOH (10 N). The mixture is extracted with dichloromethane (100 mL). The combined organic phase is dried over K$_2$CO$_3$ and then concentrated to dryness to afford (6bR, 10aS)-3-methyl-d$_3$-2,3,6b,7,8,9,10,10a-octahydro-1H-pyrido[3',4':4,5]pyrrolo[1,2,3-de]quinoxaline as a brown oil, which is used directly in the next step without further purification. MS (ESI) m/z 233.2 [M+H]$^+$.

A suspension of (6bR,10aS)-3-methyl-d$_3$-2,3,6b,7,8,9,10,10a-octahydro-1H-pyrido[3',4':4,5]pyrrolo[1,2,3-de]quinoxaline (1.6 g, 6.89 mmol), K$_2$CO$_3$ (2.0 g), KI (1.7 g) and 4-chloro-4'-fluorobutyrophenone (2.3 mL) in 3-pentanone (80 mL) is degassed by bubbling Argon for 10 min. After N, N-diisopropylethylamine (1.2 mL, 6.89 mmol) is added, the reaction mixture is stirred at 75° C. for 36 h. After the mixture is cooled to room temperature, the solvent is removed. The residue is suspended in dichloromethane (500 mL) and then is washed with H$_2$O twice (160 mL). The organic phase is dried over K$_2$CO$_3$ and then evaporated to dryness. The residue is purified by silica gel flash chromatography using a gradient of 0-100% ethyl acetate in a mixture of ethyl acetate and methanol (10:1) with 1% TEA as an eluent to afford 1-(4-fluorophenyl)-4-((6bR,10aS)-3-methyl-d$_3$-2,3,6b,7,10,10a-hexahydro-1H-pyrido[3',4':4,5]pyrrolo[1,2,3-de]quinoxalin-8(9H)-yl)butan-1-one as a brown oil (1.66 g, 61% yield). MS (ESI) m/z 397.2 [M+H]$^+$.

To a solution of 1-(4-fluorophenyl)-4-((6bR,10aS)-3-methyl-d$_3$-2,3,6b,7,10,10a-hexahydro-1H-pyrido[3',4':4,5]pyrrolo[1,2,3-de]quinoxalin-8(9H)-yl)butan-1-one (1.52 g, 3.83 mmol) in isopropyl alcohol (5.4 mL) is slowly added a solution of p-toluenesulfonic acid monohydrate (656 mg, 3.45 mmol) in 2.1 mL of isopropyl alcohol at room temperature. The reaction mixture is stirred at room temperature until a gel-like suspension is formed. Isopropyl alcohol (5.0 mL) is added and the mixture is stirred at room temperature for additional 2 h. After filtration, the filter cake is washed with isopropyl alcohol (2.5 mL). The cake is dried under vacuum to yield the title compound as a white powder (1.75 g, 80% yield). $^1$H NMR (500 MHz, DMSO-d$_6$) b 9.1 (s, 1H), 8.1 (ddd, J=2.73, 5.44, 8.68 Hz, 2H), 7.6-7.4 (m, 2H), 7.4-7.3 (m, 2H), 7.1 (d, J=7.81 Hz, 2H), 6.6 (t, J=7.62 Hz, 1H), 6.4 (d, J=7.89 Hz, 1H), 3.6 (dd, J=6.34, 12.15 Hz, 1H), 3.5-3.4 (m, 3H), 3.4-3.3 (m, 2H), 3.3-3.2 (m, 1H), 3.2-3.0 (m, 5H), 2.7 (td, J=3.04, 10.27 Hz, 1H), 2.7-2.5 (m, 1H), 2.3 (s, 3H), 2.3-2.2 (m, 1H), 2.0 (m, 3H).

Example 2

2,2-D$_2$-1-(4-fluorophenyl)-4-((6bR,10aS)-3-methyl-2,3,6b,7,10,10a-hexahydro-1H-pyrido[3',4':4,5]pyrrolo[1,2,3-de]quinoxalin-8(9H)-yl)butan-1-one

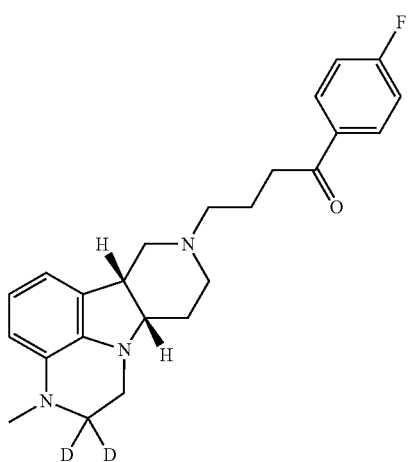 [SMILES: [2H]C1([2H])CN2c3c(cccc3N1C)[C@@H]1CN(CCCC(=O)c3ccc(F)cc3)CC[C@@H]12]

To a suspension of (6bR, 10aS)-3-Methyl-2-oxo-2,3,6b,9,10,10a-hexahydro-1H,7H-pyrido[3',4':4,5]pyrrolo[1,2,3-de]quinoxaline-8-carboxylic acid ethyl ester (945 mg, 3 mmol) in THF (5 mL) is slowly added BD$_3$-THF (1.0 M in THF, 10 mL, 10 mmol) at room temperature. After completion of the addition, the reaction mixture is stirred at room temperature overnight and then carefully quenched with D$_2$O (2.0 mL). The solvent is removed under vacuum and the residue is suspended in HCl (12 N, 9 mL). After stirred at 95° C. for 20 h, the reaction mixture is cooled to room temperature and then adjusted to pH of 12 with 50% NaOH. The mixture is concentrated to dryness to give 2,2-d$_2$-(6bR, 10aS)-3-Methyl-2,3,6b,7,8,9,10,10a-octahydro-1H-pyrido[3',4':4,5]pyrrolo[1,2,3-de]quinoxaline as a brown solid, which is used directly for next step without further purification. MS (ESI) m/z 232.2 [M+H]$^+$.

To a solution of 2,2-d$_2$-(6bR, 10aS)-3-methyl-2,3,6b,7,8,9,10,10a-octahydro-1H-pyrido[3',4':4,5]pyrrolo[1,2,3-de]quinoxaline (200 mg, 0.87 mmol) in 3-pentanone (6 mL) is added KI (290 mg, 1.75 mmol) and 4-chloro-4'-fluorobutyrophenone (0.29 mL, 1.75 mmol), followed by N, N-diisopropylethylamine (0.16 mL, 1.75 mmol). The resulting mixture is stirred at 75° C. for 20 h. After the solvent is removed under reduced pressure, the obtained residue is purified by silica gel column chromatography using a gradient of 0-100% ethyl acetate in a mixture of ethyl acetate and methanol (10:1) with 2% TEA as an eluent to afford the title compound as a brown oil. (47 mg, 14% yield). $^1$H NMR (500 MHz, CDCl$_3$) δ 8.00 (dd, J=8.9, 5.4 Hz, 2H), 7.13 (t, J=8.6 Hz, 2H), 6.65 (t, J=7.6 Hz, 1H), 6.51 (d, J=6.6 Hz, 1H), 6.41 (d, J=7.8 Hz, 1H), 3.29 (d, J=10.1 Hz, 1H), 3.25-3.14 (m, 2H), 3.02 (t, J=7.1 Hz, 2H), 2.98-2.90 (m, 1H), 2.86 (s, 3H), 2.84-2.69 (m, 2H), 2.61-2.23 (m, 3H), 2.17-1.86 (m, 5H).). MS (ESI) m/z 396.2 [M+H]$^+$.

Example 3

2,2-D$_2$-1-(4-fluorophenyl)-4-((6bR,10aS)-3-methyl-d$_3$-2,3,6b,7,10,10a-hexahydro-1H-pyrido[3',4':4,5]pyrrolo[1,2,3-de]quinoxalin-8(9H)-yl)butan-1-one p-toluenesulfonate

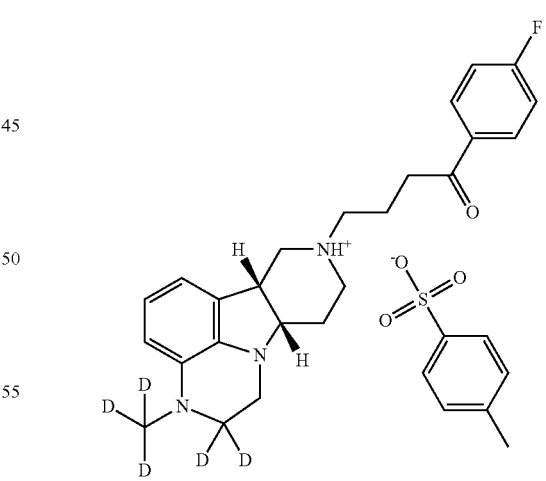

To a solution of (6bR,10aS)-ethyl 3-methyl-d$_3$-2-oxo-2,3,6b,7,10,10a-hexahydro-1H-pyrido[3',4':4,5]pyrrolo[1,2,3-de]quinoxaline-8(9H)-carboxylate solution (1.2 g, 3.77 mmol) in THF(7.0 mL) is slowly added BD$_3$-THF (10 mL, 1M in THF). The resulting mixture is stirred at room temperature overnight. CD$_3$OD (1.0 mL) is added dropwise to quench the reaction, followed by D$_2$O (2.0 mL). The solvents are removed under reduced pressure and the residue is suspended in HCl (12 N, 12 mL). The brown suspension is stirred at 95° C. for 24 h and then cooled to 0-5° C. The obtained mixture is adjusted to a pH of ≥14 with NaOH (10 N) and then extracted with dichloromethane three times (90 mL). The combined organic phase is dried over $K_2CO_3$, evaporated under reduced pressure, and then dried under vacuum to yield 2,2-$d_2$-(6bR, 10aS)-3-methyl-$d_3$-2,3,6b,7,8,9,10,10a-octahydro-1H-pyrido[3',4':4,5]pyrrolo[1,2,3-de]quinoxaline as brown oil (770 mg, 87% yield). MS (ESI) m/z 235.2 [M+H]$^+$.

A mixture of 2,2-$d_2$-(6bR, 10aS)-3-methyl-$d_3$-2,3,6b,7,8,9,10,10a-octahydro-1H-pyrido[3',4':4,5]pyrrolo[1,2,3-de]quinoxaline (500 mg 2.13 mmol), KI (720 mg, 4.34 mmol), 4-chloro-4'-fluorobutyrophenone (0.7 mL, 4.26 mmol) in DMF (14 mL) is bubbled with argon for 10 min. N,N-diisopropylethylamine (0.7 mL, 4.02 mmol) is added and the mixture is stirred at 95° C. until all of the starting material is consumed. The reaction mixture is cooled to room temperature and then concentrated under reduced pressure. The residue is suspended in dichloromethane (50 mL) and then washed with $H_2O$ (30 mL). The resulting dichloromethane solution is dried over $K_2CO_3$ and concentrated to dryness. The residue is purified by silica gel column chromatography using a gradient of 0-100% ethyl acetate in a mixture of ethyl acetate and methanol (10:1) with 1.5% TEA as eluent to afford 2,2-$d_2$-1-(4-fluorophenyl)-4-((6bR,10aS)-3-methyl-$d_3$-2,3,6b,7,10,10a-hexahydro-1H-pyrido[3',4':4,5]pyrrolo[1,2,3-de]quinoxalin-8(9H)-yl)butan-1-one as a brown oil (446 mg, 53% yield). MS (ESI) m/z 399.2 [M+H]$^+$.

2,2-$D_2$-1-(4-fluorophenyl)-4-((6bR,10aS)-3-methyl-$d_3$-2,3,6b,7,10,10a-hexahydro-1H-pyrido[3',4':4,5]pyrrolo[1,2,3-de]quinoxalin-8(9H)-yl)butan-1-one (201 mg, 0.51 mmol) is dissolved in isopropanol (2 mL). To the solution is added p-toluenesulfonic acid (86.2 mg, 0.45 mmol) in isopropanol (1 mL). The resulting clear solution is stirred at room temperature until a milky mixture is obtained. The mixture is cooled to 0-5° C. and then filtered. The filter cake is washed with cold isopropanol (2 mL) and then dried under high vacuum to give the title product as a white solid (180 mg, yield 63%). $^1$H NMR (500 MHz, DMSO-$d_6$) δ 9.1 (s, 1H), 8.0 (ddd, J=2.70, 5.52, 8.77 Hz, 2H), 7.5-7.4 (m, 2H), 7.4-7.3 (m, 2H), 7.1 (d, J=7.83 Hz, 2H), 6.4 (d, J=7.32 Hz, 1H), 3.6 (s, 1H), 3.5-3.2 (m, 5H), 3.1 (dt, J=7.74, 14.91 Hz, 4H), 2.8-2.5 (m, 1H), 2.3 (s, 4H), 2.2-1.9 (m, 4H).

Comparative Example 4

1-(4-Fluoro(2,3,5,6-$d_4$)phenyl)-4-((6bR,10aS)-3-methyl-2,3,6b,7,10,10a-hexahydro-1H-pyrido[3',4':4,5]pyrrolo[1,2,3-de]quinoxalin-8(9H)-yl)butan-1-one p-toluenesulfonate

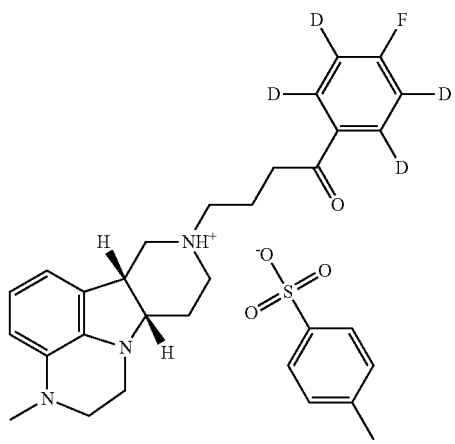

3-Pentanone (4 mL) is added into a mixture of (6bR, 10aS)-3-Methyl-2,3,6b,7,8,9,10,10a-octahydro-1H-pyrido[3',4':4,5]pyrrolo[1,2,3-de]quinoxaline (460 mg, 2.0 mmol), 2',3',5',6'-$d_4$-4-chloro-4'-fluorobutyrophenone (428 mg, 2.0 mmol), KI (335 mg, 2.0 mmol) and $K_2CO_3$ (300 mg, 2.2 mmol). The resulting mixture is bubbled with argon for 10 min and then stirred at 75° C. for 20 h. After the reaction mixture is cooled to room temperature, dichloromethane (30 mL) and $H_2O$ (15 mL) are added. The organic phase is separated and then extracted with 1N HCl solution (30 mL). The obtained aqueous phase is washed with dichloromethane (5 mL) and then added slowly to a mixture of dichloromethane (20 mL) and NaOH (50%, 10 mL) at 0-5° C. After the completion of the addition, the organic phase is separated and concentrated to dryness. The residue is further purified by basic $Al_2O_3$ column chromatography using a gradient of 0-40% ethyl acetate in hexanes as an eluent to give 1-(4-fluoro(2,3,5,6-$d_4$)phenyl)-4-((6bR,10aS)-3-methyl-2,3,6b,7,10,10a-hexahydro-1H-pyrido[3',4':4,5]pyrrolo[1,2,3-de]quinoxalin-8(9H)-yl)butan-1-one free base (200 mg, 25% yield). MS (ESI) m/z 398.2 [M+H]$^+$.

To the purified free base (125 mg, 0.31 mmol) in isopropanol (2 mL) is added p-toluenesulfonic acid (52 mg, 0.28 mmol) in isopropanol (1 mL) at room temperature. The resulting clear solution is stirred at room temperature until a milky suspension is formed. The solution is cooled to 0-5° C. and then filtered. The filter cake is washed with cold isopropanol (2 mL) and then dried under vacuum to give the title compound as a white solid (120 mg, 68% yield). $^1$H NMR (500 MHz, DMSO-$d_6$) δ 9.1 (s, 1H), 7.6-7.4 (m, 2H), 7.1 (d, J=7.82 Hz, 2H), 6.6 (t, J=7.64 Hz, 1H), 6.5 (d, J=7.30 Hz, 1H), 6.4 (d, J=7.87 Hz, 1H), 3.6 (dd, J=6.36, 12.51 Hz, 1H), 3.5-3.4 (m, 3H), 3.4-3.3 (m, 2H), 3.3-3.2 (m, 1H), 3.2-3.0 (m, 5H), 2.8 (s, 3H), 2.7 (td, J=2.95, 10.27 Hz, 1H), 2.7-2.5 (m, 1H), 2.3 (s, 3H), 2.3 (d, J=15.10 Hz, 1H), 2.1-1.9 (m, 3H).

Example 5: Measurement of Parent and Metabolite Levels in Mice

The compounds of Examples 1 to 3 and the compound of Formula Q are dosed in mice, and the levels of the both the parent compounds and the major amide metabolites are studied. Procedures for the synthesis of the compound of Formula Q can be found in WO 2008/112280. The compound of Comparative Example 4 is used as an internal standard in each study in order to control for differences in the inherent rate of metabolism in each study's animal group. After single dose oral administration of the test compound and the internal standard, plasma levels of the parent compounds and metabolites are measured at 0.25, 0.5, 1, 2, 4 and 6 hours. The maximum concentration, time to maximum concentration, and Area Under the Curve (AUC) for both the parent and the major amide metabolite is determined. The AUC value for each test compound is normalized by taking its ratio to the AUC of the internal standard (Ex. 4). Relative Amide Formation is thus calculated as follows for each Example X (i.e., Ex. 1, Ex. 2, Ex. 3 and Ex. Q):

$$\text{Relative Amide Formation}(\text{Ex. X}) = \frac{AUC_{X-Parent}/AUC_{X-Amide}}{AUC_{Std-Parent}/AUC_{Std-Amide}}$$

The results are summarized in Table 1 below.

| | Compound | Relative Amide Formation |
|---|---|---|
| Study 1 | Ex. 1 | 0.54 |
| Study 2 | Ex. 2 | 0.38 |

-continued

| | Compound | Relative Amide Formation |
|---|---|---|
| Study 3 | Ex. 3 | 0.31 |
| Study 4 | Q | 0.79 |

It is found that the extent of conversion of the parent compound to the amide metabolite is considerably lower for the compounds of Example 1, 2 and 3 compared to the non-deuterated compound of Formula Q. After normalizing for the extent of metabolism of the internal standard, it is found that the extent of amide formation for the compounds of Examples 1, 2 and 3 is significantly lower than for the non-deuterated compound Q Receptor binding studies indicate that the compounds of Example 1, Example 2 and Example 3 show substantially the same receptor binding profile as the non-deuterated compound of Formula Q (including, e.g., serotonin receptor (e.g., 5-HT$_2$A), dopamine receptor (e.g., D2) and serotonin transporter binding). For example, the compound of Example 2 shows 98% inhibition of the human serotonin 5-HT$_2$A receptor at a concentration of 0.1 µM.

Example 6: Comparison of Pharmacokinetics Between Deuterated and Non-Deuterated Compounds in Rats In vivo metabolism (demethylation/oxidation) of the deuterated Compound of Example 2 (the Compound of Formula I, tosylate salt) is compared to that of its non-deuterated congener, the Compound of Formula Q (tosylate salt). The pharmacokinetics of each compound is determined after both oral (PO) and intravenous (IV) administration in crossover studies in rats.

PO Administration: Six male Sprague-Dawley rats are divided into two 3-rat groups for PO administration of compound on day 1 of the study. Rats in group 1 are administered 10 mg/kg (free base equivalent) of the Compound of Formula Q, while rats in group 2 are administered 10 mg/kg (free base equivalent) of the Compound of Example 2. Blood samples are collected at 0.25, 0.5, 1, 2, 4, 6, 8, 12 and 24-hours post dose and analyzed for plasma concentration of the administered compound and its metabolites. Following a three-day wash out period, the rats of group 1 and group 2 are crossed over and administered, respectively, 10 mg/kg (free base equivalent) of the Compound of Example 2 and 10 mg/kg (free base equivalent) of the Compound of Formula Q. Blood samples are collected and analyzed as described above, except that an additional sample is taken pre-dose.

IV Administration: Six male Sprague-Dawley rats are divided into two 3-rat groups for IV administration of compound on day 1 of the study. Rats in group 1 are administered 1 mg/kg (free base equivalent) of the Compound of Formula Q, while rats in group 2 are administered 1 mg/kg (free base equivalent) of the Compound of Example 2. Blood samples are collected at 2 minutes, 5 minutes, 0.25, 0.5, 2, 4, 6, 8 and 12 hours post dose and analyzed for plasma concentration of the administered compound and its metabolites. Following a 72-hour wash out period, the rats of group 1 and group 2 are crossed over and administered, respectively, 1 mg/kg (free base equivalent) of the Compound of Example 2 and 1 mg/kg (free base equivalent) of the Compound of Formula Q. Blood samples are collected and analyzed as described above, except that an additional sample is taken pre-dose.

All blood samples are processed to plasma and analyzed for parent and metabolite concentrations using liquid chromatography-tandem mass spectrometry (LC-MS/MS). The metabolites analyzed include the N-demethylated amide compound Q-1 (discussed supra). Area under the curve (AUC) of parent and metabolites based on plasma versus time data are calculated using Prism 5.04 software (GraphPad Software, Inc.).

The results are summarized in Table 2 below (AUC is shown for 0-24 hours, measured in ng-hr/mL):

| | Test Compound: | Formula Q | Example 2 (Formula I) |
|---|---|---|---|
| PO | Parent AUC | 56.0 | 58.5 |
| | Metabolite Q-1, AUC | 128.2 | 67.8 |
| IV | Parent AUC | 230.6 | 257.2 |
| | Metabolite Q-1, AUC | 6.7 | 3.7 |

It is found that after PO dosing of the Compound of Formula Q, the parent compound is extensively metabolized, with extensive formation of the N-demethylated/alpha-oxidized amide (Formula Q-1). The AUC of the metabolite Q-1 is 2.2-fold higher than the AUC of the parent. In contrast, IV dosing resulted in much less extensive metabolism. After IV administration, the Q-1 metabolite AUC is only about 2% of that of the parent. This demonstrates a high degree of first-pass (hepatic) metabolism that proceeds predominantly by way of N-demethylation and alpha-N oxidation.

In contrast, PO dosing of the Compound of Example 2 results in significantly less metabolism to the metabolite Q-1 compared to its non-deuterated congener. The AUC of the metabolite Q-1 is only 1.2-fold higher than the AUC of the parent, compared to 2.2-fold higher in the case of administration of the Compound of Formula Q. Thus, there is a 55% decrease in relative metabolism to the demethylated amide derivative. Similar results are obtained for IV administration, wherein the Q-1 metabolite AUC is found to be about 1% of that of the parent. It is also shown that when comparing the plasma AUC from equivalent PO dosing of the Compound of Formula Q to the Compound of Example 2, the latter results in approximately half the plasma AUC of metabolite Q-1 (67.8 ng-hr/mL vs. 128.2 ng-hr/mL).

Example 7: Comparison of Pharmacokinetics Between Deuterated and Non-Deuterated Compounds in Dogs In vivo metabolism (demethylation and alpha-oxidation) of the deuterated Compound of Example 2 (the Compound of Formula I, tosylate salt) is compared to that of its non-deuterated congener, the Compound of Formula Q (tosylate salt). The pharmacokinetics of each compound is determined after both sublingual (SL) and subcutaneous (SC) administration in non-cross over sequential studies in dogs.

SC Administration: Six male beagle dogs between 2 and 5 years of age are randomized in two groups of three dogs each. Dogs in group 1 are administered the compound of Formula Q at a dose of 1 mg/kg (free base equivalent) in a 0.5% methylcellulose/distilled water vehicle. Dogs in group 2 are administered the compound of Example 2 at a dose of 1 mg/kg (free base equivalent) in a 0.5% methylcellulose/distilled water vehicle. Administration is subcutaneous in the intrascapular region via a 22 or 23 gauge needle. Whole blood samples are collected via the dog's cephalic vein pre-dose, and at post-dose time-points 5, 15 and 30 minutes, 1, 2, 4, 6, 8 and 24 hours. Following a minimum 7-day washout period, the dogs are transferred to the sublingual portion of the study.

SL Administration: The dogs of group 1 are administered the compound of Formula Q at a dose of 1 mg/kg (free base equivalent) in a 0.5% methylcellulose/distilled water vehicle. Dogs in group 2 are administered the compound of Example 2 at a dose of 1 mg/kg (free base equivalent) in a 0.5% methylcellulose/distilled water vehicle. The animals are anesthetized prior to administration of the dose using propofol (6 mg/kg) and anesthesia is maintained for 30 minutes using 3-4.5% isoflurane. Administration is sublingual and the dosage is applied for 30 minutes, then wiped off using unwoven gauze. Whole blood samples are collected via the dog's cephalic vein pre-dose, and at post-dose time-points 5, 15 and 30 minutes, 1, 2, 4, 6, 8, 24, 36 and 48 hours.

All blood samples are processed to plasma and analyzed for parent and metabolite concentrations using liquid chromatography-tandem mass spectrometry (LC-MS/MS). The metabolites analyzed include the N-demethylated compound Q-1A (shown below), and the N-demethylated/alpha-oxidized amide compound Q-1 (discussed supra). Area under the curve (AUC) of parent and metabolites based on plasma versus time data are calculated using Prism 5.04 software (GraphPad Software, Inc.).

The results are summarized in Table 2 below (AUC is shown for 0-24 hours, measured in ng-hr/mL):

|    | Test Compound:     | Formula Q | Example 2 (Formula I) |
|----|--------------------|-----------|------------------------|
| SL | Parent AUC         | 734       | 1262                   |
|    | Metabolite Q-1A, AUC | 23      | 103                    |
|    | Metabolite Q-1, AUC  | N.Q.    | N.D.                   |
| SC | Parent AUC         | 813       | 785                    |
|    | Metabolite Q-1A, AUC | 20      | 49                     |
|    | Metabolite Q-1, AUC  | N.D.    | N.D.                   |

It is found that SL dosing of the compound of Example 2 results in about 72% higher parent AUC compared to dosing of the compound of Formula Q. AUC of the des-methyl metabolite Q-1A is about 3% of parent for the compound of Formula Q, and about 8% of that of the parent for the compound of Example 2. The concentration of the amide metabolite Q-1 is detectable at less than 1 ng/mL at each time point for SL administration of the compound of Formula Q (AUC not quantified), but is undetectable for SL administration of the compound of Example 2 (<0.1 ng/mL).

In contrast, SC dosing resulted in more comparable results between the two compounds. For the compound of Formula Q, the Q-1A metabolite AUC is about 3% of parent, while for the of the compound of Example 2, the Q-1A metabolite AUC is about 6% of parent. For SC dosing, the metabolite Q-1 was undetectable (<0.1 ng/mL) for both compounds. The AUC of parent is found to be comparable between the deuterated and non-deuterated compounds.

Comparing the SC to SL results, for the compound of Formula Q, SL administration resulted in 10% less net AUC of parent compound compared to SC administration. In contrast, dosing the deuterated compound of Example 2 leads to 61% higher parent AUC for SL compared to SC. Without being bound by theory, it is believed that this difference is related to differences in the rate of absorption from the subcutaneous space between the deuterated and non-deuterated species.

Taken together, these results show that deuteration of the methylene group adjacent to the piperazine nitrogen reduced metabolism of the compound of the invention compared to its non-deuterated analog, resulting in higher and more prolonged plasma concentrations of the parent drug. Since the concentration of the de-methylated Q-1 A metabolite is found to be higher for the deuterated compound, compared to the non-deuterated compound, the results suggest, as seen in rats, that deuteration is inhibiting the subsequent oxidation of the de-methylated amine to its amide derivative (Q-1).

The formation of the metabolite Q-1 is believed to occur by way of the intermediate metabolite Q-1A, shown below:

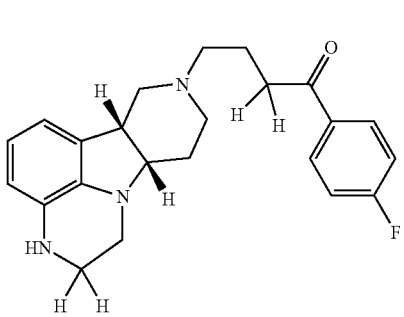

Formula Q-1A

Thus, the parent compound Q undergoes de-methylation to an amine followed by oxidation of the methylene adjacent to the amine to form the amide metabolite, Q-1A. The results presented in Examples 6 and 7 demonstrate that for both dogs and rats, deuteration of the Compound of Formula Q at the indicated position, to yield the Compound of Example 2, significantly decreases oxidation of the N-methyl piperazine moiety, thus indicating blockage of this metabolic pathway.

The reduction in metabolism of the parent compound Q to the Q-1 metabolite can have important clinical consequences, because the parent compound Q, the Q-1 metabolite and the Q-1A metabolites are all known to be pharmacologically active species, but with different receptor selectivity profiles. For example, Table 2 summarizes some of the receptor activity distinctions between these species (measurements are Ki (nM)):

| Receptor              | Cmpd. Q | Cmpd. Q-1A | Cmpd. Q-1 |
|-----------------------|---------|------------|-----------|
| Serotonin 5-HT$_{2A}$ | 0.54    | 2          | 11        |
| Dopamine D2           | 32      | 30         | 50-250    |
| Dopamine D1           | 52      | 110        | 22        |
| Serotonin Transporter | 33-72   | 31-78      | >600      |

Table 2 shows that while all three compounds activity at the serotonin, dopamine D1, dopamine D2 and serotonin transporter receptors, their relative activities at these receptors varies. While the metabolite Q-1A has a largely similar pharmacologic profile to the parent Q, Table 2 shows that the metabolite Q-1 diverges significantly in that there is much less relative activity at the Dopamine D2 receptor and at the serotonin transporter. In addition, the compound of formula Q-1, unlike Q and Q-1A, has been found to be a potent mu opiate receptor antagonist (Ki of about 22 nM). Because of their different receptor activity profiles, each of the relevant metabolites has distinct functional pharmacological effects compared to the parent drug Q. Thus, by blocking the metabolism pathway which converts the compounds Q and Q-JA to the metabolite Q-1, a significant effect on pharmacological function can result. The present invention is therefore useful in inhibiting this metabolic pathway in order to modulate overall pharmacological profile provided by the parent drugs.

The invention claimed is:

1. A method for the treatment of bipolar disorder or bipolar depression comprising administering to a patient in need thereof a therapeutically effective amount of the compound of formula I, Formula I

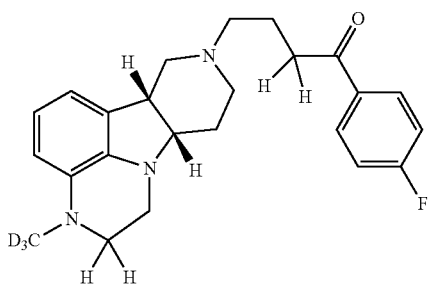

in free or salt form, or
the compound of formula II,

Formula II

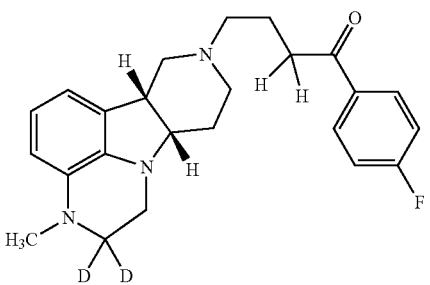

in free or salt form, or
the compound of formula III,

Formula III

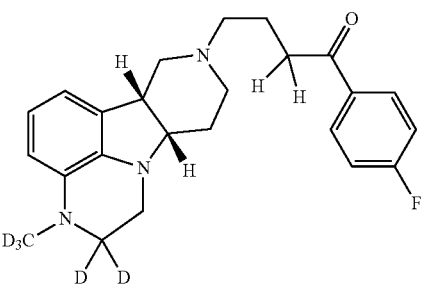

in free or salt form.

2. The method according to claim 1, wherein said compound is in salt form.

3. The method according to claim 2, wherein the salt is a toluenesulfonic acid addition salt.

4. The method according to claim 1, wherein the compound is the compound of Formula II in free or salt form.

5. The method according to claim 1, wherein bipolar disorder is bipolar disorder with psychotic symptoms.

6. The method according to claim 1, wherein the effective amount is 2.5 mg-50 mg per day, measured as the free base equivalent.

7. The method according to claim 6, wherein the effective amount is 1 mg-40 mg per day, measured as the free base equivalent.

8. The method according to claim 1, wherein the compound is administered by injection for sustained or delayed release.

9. The method according to claim 1, wherein the method further comprises the administration of one or more other therapeutic agents.

10. The method according to claim 9, wherein the one or more other therapeutic agents are selected from compounds that modulate GABA activity, a GABA-B agonist, a 5-HT modulator, a melatonin agonist, an ion channel modulator, a serotonin-2 antagonist/reuptake inhibitor (SARIs), a $5\text{-}HT_6$ antagonist, an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug; and antipsychotic agents; in free or pharmaceutically acceptable salt form.

11. The method according to claim 10, wherein the one or more other therapeutic agents are anti-depressive agents selected from one or more of amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelazine sulfate, protriptyline, sertraline, tranylcypromine, trazodone, trimipramine, and venlafaxine.

12. The method according to claim 9, wherein the one or more other therapeutic agents are anti-depressive agents, and wherein said anti-depressive agents are selective serotonin re-uptake inhibitors.

13. The method according to claim 1, wherein the patient does not respond to a selective serotonin re-uptake inhibitor.

14. The method according to claim 13, wherein the selective serotonin re-uptake inhibitor is selected from one or more of citalopram, dapoxetine, escitalopram, fluoxetine, fluvoxamine, indalpine, paroxetine, sertraline, vilazodone, and zimelidine.

15. The method according to claim 1, wherein the patient is also receiving a selective serotonin re-uptake inhibitor.

16. The method according to claim 15, wherein the selective serotonin re-uptake inhibitor is selected from one or more of citalopram, dapoxetine, escitalopram, fluoxetine, fluvoxamine, indalpine, paroxetine, sertraline, vilazodone, and zimelidine.

17. The method according to claim 1, wherein the compound has greater than 90% incorporation of deuterium at the indicated deuterium positions of the structure.

18. The method according to claim 1, wherein the compound has greater than 97% incorporation of deuterium, at the indicated deuterium positions of the structure.

19. The method according to claim 1, wherein the therapeutically effective amount of the compound of Formula I or the compound of Formula II or the compound of Formula III is comprised in a pharmaceutical composition for sustained or delayed release, which is formulated for administration by injection, and which comprises the compound of Formula I or II or III dispersed or dissolved in a polymeric matrix.

20. The method according to claim 19, wherein the polymeric matrix comprises polylactide, poly-d,l-lactide, polyglycolide, or a poly(d,l-lactide-co-glycolide) copolymer (PLGA).

21. The method according to claim 20, wherein the polymeric matrix comprises a poly(d,l-lactide-co-glycolide) copolymer (PLGA).

22. The method according to claim 21, wherein the PLGA copolymer has a lactide to glycolide ratio from 50:50 to 90:10.

23. The method according to claim 21, wherein the PLGA copolymer is selected from PLGA 50:50, PLGA 75:25, PLGA 85:15, and PLGA 90:10.

24. The method according to claim 21, wherein the PLGA copolymer has a weight-average molecular weight from 5,000 to 500,000 daltons.

25. The method according to claim 1, wherein the compound is the compound of Formula I in free or salt form.

26. The method according to claim 25, wherein said compound is in salt form.

27. The method according to claim 26, wherein the salt is a toluenesulfonic acid addition salt.

28. The method according to claim 4, wherein the salt is a toluenesulfonic acid addition salt.

29. The method according to claim 1, wherein the compound is the compound of Formula III in free or salt form.

30. The method according to claim 29, wherein said compound is in salt form.

31. The method according to claim 30, wherein the salt is a toluenesulfonic acid addition salt.

32. The method according to claim 19, wherein the compound is the compound of Formula II in free or toluenesulfonic acid addition salt form.

33. The method according to claim 21, wherein the compound is the compound of Formula II in free or toluenesulfonic acid addition salt form.

34. The method according to claim 22, wherein the compound is the compound of Formula II in free or toluenesulfonic acid addition salt form.

* * * * *

UNITED STATES PATENT AND TRADEMARK OFFICE
CERTIFICATE OF CORRECTION

PATENT NO. : 11,723,909 B2
APPLICATION NO. : 17/379399
DATED : August 15, 2023
INVENTOR(S) : Yao et al.

It is certified that error appears in the above-identified patent and that said Letters Patent is hereby corrected as shown below:

In the Specification

Column 9, Line 32, "Method 1" should be changed to "Method I"

Column 11, Line 54, "Nonnud" should be changed to "Normud"

Column 13, Line 20, "Method 1" should be changed to "Method I"

Column 13, Line 36, "Method 1" should be changed to "Method I"

Column 15, Line 25, "Method 1-A or 11-A" should be changed to "Method I-A or II-A"

Column 15, Line 63, "GlaxoSnithKline" should be changed to "GlaxoSmithKline"

Column 16, Line 1, "Method I-A or TI-A" should be changed to "Method I-A or II-A"

Column 16, Line 36, "Method T-A or IT-A" should be changed to "Method I-A or II-A"

Column 17, Line 16, "Method I-A or 11-A" should be changed to "Method I-A or II-A"

Column 18, Line 32, "Methods $I_P$-A, IL-A" should be changed to "Methods $I_P$-A, II-A"

Column 18, Line 52, "clonipramine" should be changed to "clomipramine"

Column 18, Line 54, "fluvoxanine" should be changed to "fluvoxamine"

Column 19, Line 18, "adrafRnil" should be changed to "adrafinil"

Column 19, Line 58, "Method 11" should be changed to "Method II"

Signed and Sealed this
Fifth Day of December, 2023

Katherine Kelly Vidal
*Director of the United States Patent and Trademark Office*

CERTIFICATE OF CORRECTION (continued)
U.S. Pat. No. 11,723,909 B2

Column 27, Line 34, "b 9.1" should be changed to "δ 9.1"

Column 33, Line 62, "Q-1 A metabolite" should be changed to "Q-1A metabolite"

Column 34, Lines 56-57, "Q and Q-JA" should be changed to "Q and Q-1A"